(12) United States Patent
Scholz et al.

(10) Patent No.: US 9,381,127 B2
(45) Date of Patent: Jul. 5, 2016

(54) PATIENT SUPPORT SYSTEMS AND METHODS FOR TRANSFERRING PATIENTS AND CONTROLLING PATIENT TEMPERATURE

(76) Inventors: Matthew T. Scholz, Woodbury, MN (US); Hatim M. Carim, West Saint Paul, MN (US); Brent R. Hansen, New Richmond, WI (US)

(*) Notice: Subject to any disclaimer, the term of this patent is extended or adjusted under 35 U.S.C. 154(b) by 645 days.

(21) Appl. No.: 13/577,945

(22) PCT Filed: Feb. 25, 2011

(86) PCT No.: PCT/US2011/026177
§ 371 (c)(1),
(2), (4) Date: Aug. 9, 2012

(87) PCT Pub. No.: WO2011/106600
PCT Pub. Date: Sep. 1, 2011

(65) Prior Publication Data
US 2012/0304384 A1  Dec. 6, 2012

Related U.S. Application Data

(60) Provisional application No. 61/308,628, filed on Feb. 26, 2010.

(51) Int. Cl.
*A61G 7/10* (2006.01)
(52) U.S. Cl.
CPC ............ *A61G 7/1025* (2013.01); *A61G 7/1021* (2013.01); *A61G 2203/90* (2013.01); *A61G 2210/90* (2013.01)
(58) Field of Classification Search
CPC . A61G 2200/32; A61G 7/05746; A61G 1/01; A61G 1/044; A61G 7/05753; A61G 7/05769; A61G 7/1025; A61G 2203/90; A61G 7/1021; A61G 2210/90; A47C 7/742
See application file for complete search history.

(56) References Cited

U.S. PATENT DOCUMENTS

| | | | |
|---|---|---|---|
| 3,422,648 A | 1/1969 | Lemelson | |
| 3,586,220 A | 6/1971 | Reinsberg | |

(Continued)

FOREIGN PATENT DOCUMENTS

| | | | | |
|---|---|---|---|---|
| GB | 2265826 A | * | 10/1993 | ............. A47C 27/10 |
| JP | 61-60933 U | | 4/1986 | |

(Continued)

OTHER PUBLICATIONS

"Transfer Assist Devices for the Safer Handling of Patients—A Guide for Selection and Safe Use," Workers' Compensation Board of British Columbia, 22 pages.

(Continued)

*Primary Examiner* — David E Sosnowski
*Assistant Examiner* — Eric Kurilla

(57) ABSTRACT

Patient support systems and methods for transferring patients and controlling patient temperature. The system can include a non-inflatable and self-supporting platform that can include a first surface and a second surface separated by a distance, a plurality of supporting structures that extends at least partially across the distance between the first surface and the second surface, a plenum, and a plurality of apertures formed through at least one of the first surface and the second surface and in fluid communication with the plenum. The system can further include a fluid source configured to move fluid into the plenum and out the plurality of apertures. A method of transferring a patient can include moving fluid into the plenum and out the plurality of apertures to form a fluid pallet. A method of controlling patient temperature can include moving a temperature-controlled fluid into the plenum and out the plurality of apertures.

30 Claims, 6 Drawing Sheets

(56) References Cited

U.S. PATENT DOCUMENTS

| | | | | |
|---|---|---|---|---|
| 3,775,782 A | * | 12/1973 | Rice et al. | 5/625 |
| 3,778,848 A | * | 12/1973 | Lyytinen | 4/561.1 |
| 3,870,450 A | * | 3/1975 | Graebe | 425/269 |
| 3,948,344 A | | 4/1976 | Johnson | |
| 4,149,285 A | * | 4/1979 | Stanton | 5/689 |
| 4,155,421 A | | 5/1979 | Johnson | |
| 4,187,068 A | | 2/1980 | Vassar | |
| 4,205,880 A | * | 6/1980 | Trotman et al. | 297/452.45 |
| 4,234,982 A | * | 11/1980 | Bez et al. | 5/702 |
| 4,254,518 A | * | 3/1981 | Buhren et al. | 5/702 |
| 4,272,856 A | | 6/1981 | Wegener | |
| 4,391,009 A | * | 7/1983 | Schild et al. | 5/713 |
| 4,517,690 A | | 5/1985 | Wegener | |
| 4,528,704 A | | 7/1985 | Wegener | |
| 4,534,078 A | * | 8/1985 | Viesturs et al. | 5/681 |
| 4,572,188 A | | 2/1986 | Augustine | |
| 4,637,083 A | | 1/1987 | Goodwin | |
| 4,686,719 A | | 8/1987 | Johnson | |
| 4,694,521 A | * | 9/1987 | Tominaga | 5/689 |
| 4,766,629 A | * | 8/1988 | Schueler | 5/665 |
| 4,768,249 A | * | 9/1988 | Goodwin | 5/713 |
| 4,882,800 A | * | 11/1989 | Schueler | 5/665 |
| 4,894,060 A | | 1/1990 | Nestegard | |
| 4,896,389 A | * | 1/1990 | Chamberland | 5/710 |
| 4,905,331 A | | 3/1990 | Hochschild | |
| 4,964,183 A | * | 10/1990 | LaForce, Jr. | 5/421 |
| 5,035,014 A | * | 7/1991 | Blanchard | 5/424 |
| 5,065,464 A | | 11/1991 | Blanchard | |
| 5,067,189 A | | 11/1991 | Weedling | |
| 5,226,188 A | * | 7/1993 | Liou | 5/653 |
| 5,329,655 A | * | 7/1994 | Garner | 5/81.1 T |
| 5,402,542 A | | 4/1995 | Viard | |
| 5,483,709 A | | 1/1996 | Foster | |
| 5,493,742 A | * | 2/1996 | Klearman | 5/423 |
| 5,513,406 A | | 5/1996 | Foster | |
| RE35,299 E | | 7/1996 | Weedling | |
| 5,561,873 A | * | 10/1996 | Weedling | 5/713 |
| 5,615,425 A | * | 4/1997 | Corente | 5/81.1 T |
| 5,815,864 A | * | 10/1998 | Sloop | 5/706 |
| 5,887,304 A | * | 3/1999 | von der Heyde | 5/726 |
| 5,890,245 A | * | 4/1999 | Klearman et al. | 5/714 |
| 5,926,883 A | * | 7/1999 | Rechin et al. | 5/706 |
| 6,052,853 A | | 4/2000 | Schmid | |
| 6,073,289 A | * | 6/2000 | Bolden et al. | 5/689 |
| 6,073,291 A | | 6/2000 | Davis | |
| 6,085,372 A | * | 7/2000 | James et al. | 5/713 |
| 6,106,922 A | | 8/2000 | Cejka | |
| 6,210,428 B1 | | 4/2001 | Augustine | |
| 6,277,144 B1 | | 8/2001 | Tomic-Edgar | |
| 6,375,674 B1 | | 4/2002 | Carson | |
| 6,421,859 B1 | | 7/2002 | Hicks | |
| 6,487,739 B1 | * | 12/2002 | Harker | 5/726 |
| 6,493,888 B1 | * | 12/2002 | Salvatini et al. | 5/423 |
| 6,497,720 B1 | | 12/2002 | Augustine | |
| 6,658,676 B1 | * | 12/2003 | Persson et al. | 5/81.1 HS |
| 6,761,682 B2 | | 7/2004 | Goldberg | |
| 7,007,330 B2 | | 3/2006 | Kuiper | |
| 7,014,431 B2 | | 3/2006 | Hansen | |
| 7,176,419 B2 | | 2/2007 | Ellis | |
| 7,210,176 B2 | | 5/2007 | Weedling | |
| 7,243,382 B2 | | 7/2007 | Weedling | |
| 7,338,515 B2 | | 3/2008 | Van Duren | |
| 7,735,164 B1 | * | 6/2010 | Patrick | 5/81.1 HS |
| 2002/0166168 A1 | | 11/2002 | Weedling | |
| 2003/0159212 A1 | | 8/2003 | Patrick | |
| 2005/0028273 A1 | | 2/2005 | Weedling | |
| 2005/0034229 A1 | | 2/2005 | Weedling | |
| 2005/0102749 A1 | | 5/2005 | Heimbrock | |
| 2005/0193496 A1 | | 9/2005 | Weedling | |
| 2005/0246833 A1 | * | 11/2005 | Barth et al. | 5/81.1 R |
| 2005/0246834 A1 | | 11/2005 | Weedling | |
| 2006/0000016 A1 | | 1/2006 | Weedling | |
| 2006/0010607 A1 | * | 1/2006 | Schneider | 5/713 |
| 2006/0037136 A1 | | 2/2006 | Weedling | |
| 2006/0156468 A1 | | 7/2006 | Patrick | |
| 2006/0162086 A1 | | 7/2006 | Davis | |
| 2006/0253976 A1 | | 11/2006 | Weedling | |
| 2007/0006385 A1 | | 1/2007 | Davis | |
| 2007/0107133 A1 | * | 5/2007 | Schwaiger et al. | 5/713 |
| 2008/0016618 A1 | | 1/2008 | O'Shea | |
| 2009/0064416 A1 | | 3/2009 | Kummer | |
| 2009/0265856 A1 | * | 10/2009 | Xu | A47L 23/266 5/699 |
| 2012/0124752 A1 | * | 5/2012 | Patrick | 5/703 |
| 2012/0284918 A1 | * | 11/2012 | Gazagnes | 5/421 |
| 2012/0297540 A1 | * | 11/2012 | Thomas et al. | 5/424 |

FOREIGN PATENT DOCUMENTS

| | | |
|---|---|---|
| JP | 09-286520 | 11/1997 |
| JP | 2005-342225 | 12/2005 |
| JP | 2009-220758 | 10/2009 |
| KR | 20-0304535 | 2/2003 |
| KR | 20-0322778 | 8/2003 |
| WO | 02/062185 | 8/2002 |

OTHER PUBLICATIONS

Brochure: Kimberly-Clark Patient Warming System Thermal Pads and M1000 Control Unit, 2 pages.

Brochure: HoverTech International, 2 pages.

Bair Hugger Therapy—Underbody Series Blankets, 2 pages, http://www.arizant.com/us/bairhuggertherapy/blankets/underbody, printed Feb. 26, 2010.

Corplast Packaging Industries SDN BHD, 2 pages, http://www.corplast.com/specification.html, printed Feb. 26, 2010.

Supplementary European Search Report (EP11748115) Feb. 13, 2015; 2 pgs.

* cited by examiner

PATIENT SUPPORT SYSTEMS AND METHODS FOR TRANSFERRING PATIENTS AND CONTROLLING PATIENT TEMPERATURE

CROSS REFERENCE TO RELATED APPLICATIONS

This application is a national stage filing under 35 U.S.C. 371 of PCT/US2011/026177, filed Feb. 25, 2011, which claims priority to Provisional Application No. 61/308,628, filed Feb. 26, 2010, the disclosure of which is incorporated by reference in its/their entirety herein.

FIELD

The present disclosure generally relates to patient support systems, and particularly, to patient support systems and methods for transferring patients and/or controlling patient temperature, for example, by actively warming and/or cooling the patients.

BACKGROUND

Patients, and particularly non-ambulatory patients, in healthcare facilities, such as hospitals and nursing homes, may need to be transferred from one location to another. For example, patients may be transferred between at least one of a hospital bed, a gurney or stretcher, a surgical table in an operating room, cardiac catheterization lab, a diagnostic table (e.g., a table used during CT, MRI and/or other diagnostic evaluations), etc., and combinations thereof. For example, a patient may need to be moved from a hospital bed that must remain in a patient's room, to a gurney and then from the gurney to a treatment table, such as a surgical table. Following treatment, the reverse patient handling sequence may need to occur. Many of such patient transfers occur between surfaces at or near the same level making it a horizontal or near horizontal transfer.

In some patient transfer situations, sliding a patient along a supporting surface is minimized to avoid skin damage particularly in the elderly or patients with fragile skin as well as to avoid causing patient pain or discomfort, such as when the patient has unhealed surgical incisions. However, lifting of the patient may also need to be minimized both for patient comfort and for worker safety. In some cases, a combination of sliding and lifting may be employed, and/or multiple healthcare personnel may need to be involved in the transfer.

In addition, controlling patient temperature can be a critical element to good care. For example, patient warming devices can be used to actively warm patients or portions of patients (e.g., selectively warm) during a variety of medical procedures, such as surgeries. In such situations, the entire patient can be warmed or a portion of the patient can be warmed to avoid a potentially detrimental drop in core body temperature during a medical procedure, such as an extended surgery. In other situations, it may be beneficial to cool the patient, for example, during cardiac surgery or immediately after cardiac arrest.

SUMMARY

Some aspects of the present disclosure provide a patient support system. The patient support system can include a non-inflatable and self-supporting platform that can include a first surface and a second surface positioned substantially parallel to the first surface and separated from the first surface by a distance. The platform can further include a plurality of supporting structures that extends at least partially across the distance between the first surface and the second surface, the plurality of supporting structures being optionally coupled to at least one of the first surface and the second surface, and a plenum defined at least partially by the first surface, the second surface, and the plurality of supporting structures. The platform can further include a plurality of apertures formed through at least a portion of at least one of the first surface and the second surface and in fluid communication with the plenum. The patient support system can further include a fluid source fluidly coupled to the plenum, the fluid source being a positive pressure fluid source configured to move fluid from the fluid source into the plenum and out the plurality of apertures.

Some aspects of the present disclosure provide a method for transferring a patient. The method can include providing a patient support system comprising a non-inflatable and self-supporting platform that can include a first surface, and a second surface positioned substantially parallel to the first surface and separated from the first surface by a distance. The platform can further include a plurality of supporting structures that extend at least partially across the distance between the first surface and the second surface, the plurality of supporting structures being optionally coupled to at least one of the first surface and the second surface, and a plenum defined at least partially by the first surface, the second surface, and the plurality of supporting structures. The platform can further include a plurality of apertures formed through at least a portion of the second surface and in fluid communication with the plenum to allow fluid to exit the plenum via the plurality of apertures. The method can further include moving fluid into the plenum to fill the plenum without inflating the platform more than 200% from its nonpressured state, and moving fluid out the plurality of apertures, for example, to form a fluid pallet adjacent one of the first surface and the second surface.

Some aspects of the present disclosure provide a method for controlling the temperature of a patient. The method can include providing a patient support system comprising a non-inflatable and self-supporting platform that can include a first surface, and a second surface positioned substantially parallel to the first surface and separated from the first surface by a distance. The platform can further include a plurality of supporting structures that extend at least partially across the distance between the first surface and the second surface, the plurality of supporting structures being optionally coupled to at least one of the first surface and the second surface, and a plenum defined at least partially by the first surface, the second surface, and the plurality of supporting structures. The platform can further include a plurality of apertures formed through at least a portion of the first surface and in fluid communication with the plenum to allow fluid to exit the plenum via the plurality of apertures. The method can further include moving a temperature-controlled fluid into the plenum and out the plurality of apertures.

Some aspects of the present disclosure provide a patient support system comprising a non-inflatable and self-supporting platform that can include a first surface, and a second surface positioned substantially parallel to the first surface and separated from the first surface by a first distance. The platform can further include a first plurality of supporting structures that extends at least partially across the first distance between the first surface and the second surface, the plurality of supporting structures being optionally coupled to at least one of the first surface and the second surface, and a first plenum defined at least partially by the first surface, the second surface, and the plurality of supporting structures. The platform can further include a third surface positioned substantially parallel to the second surface and positioned opposite the first surface, the third surface separated from the second surface by a second distance, and a second plurality of supporting structures that extends at least partially across the second distance between the second surface and the third surface. The plurality of supporting structures can be optionally coupled to at least one of the second surface and the third surface. The platform can further include a second plenum defined at least partially by the third surface and the second plurality of supporting structures, and a plurality of apertures formed through at least a portion of the third surface and in fluid communication with the second plenum. The patient support system can further include a fluid source fluidly coupled to the second plenum, the fluid source being a positive pressure fluid source configured to move fluid from the fluid source into the second plenum and out the plurality of apertures.

Some aspects of the present disclosure provide a method for controlling the temperature of a patient and transferring a patient. The method can include providing a patient support system comprising a non-inflatable and self-supporting platform that can include a first surface, and a second surface positioned substantially parallel to the first surface and separated from the first surface by a first distance. The platform can further include a first plurality of supporting structures that extends at least partially across the first distance between the first surface and the second surface, the plurality of supporting structures being optionally coupled to at least one of the first surface and the second surface, and a first plenum defined at least partially by the first surface, the second surface, and the plurality of supporting structures. The platform can further include a third surface positioned substantially parallel to the second surface and positioned opposite the first surface, the third surface separated from the second surface by a second distance, and a second plurality of supporting structures that extends at least partially across the second distance between the second surface and the third surface. The plurality of supporting structures can be optionally coupled to at least one of the second surface and the third surface. The platform can further include a second plenum defined at least partially by the third surface and the second plurality of supporting structures, and a plurality of apertures formed through at least a portion of the third surface and in fluid communication with the second plenum. The method can further include providing a temperature-controlled first fluid into the first plenum, and moving fluid into the second plenum and optionally out the plurality of apertures, for example, to form a fluid pallet adjacent the third surface.

Other features and aspects of the present disclosure will become apparent by consideration of the detailed description and accompanying drawings.

DETAILED DESCRIPTION

Figure 1:
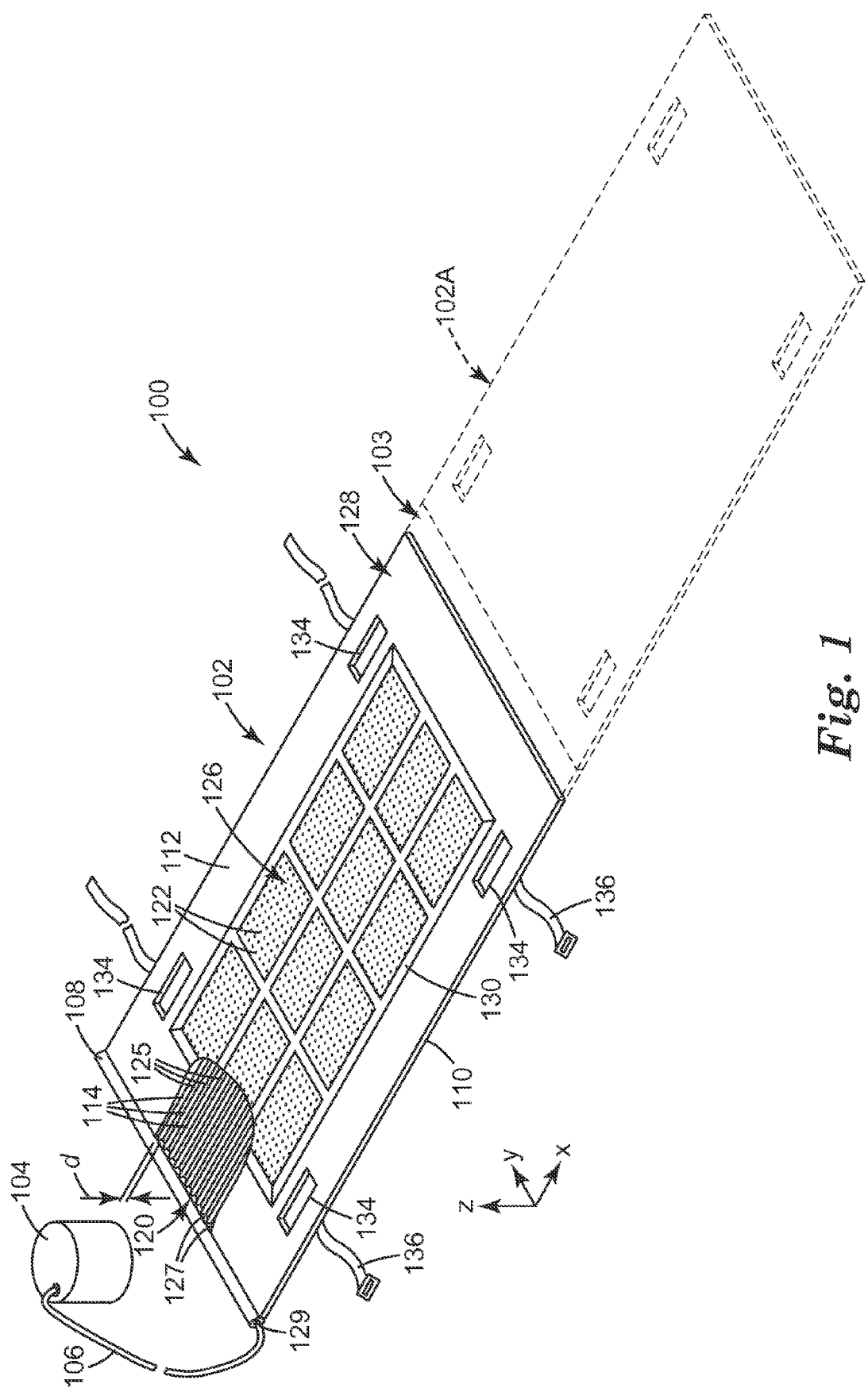
FIG. 1 is a bottom perspective view of a patient support system according to one embodiment of the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "supported," "connected," "coupled," and "fluidly coupled," and variations thereof, are used broadly and encompass both direct and indirect supports, connections, couplings, and fluid couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to patient support systems and methods for transferring patients and/or controlling the body temperature of patients, for example, by actively warming or cooling the patients. In some embodiments the patient support system can be configured only for patient transfer or patient thermal control. However, in some embodiments, the patient support system can be configured to provide either patient transfer or patient thermal control, as desired, or to provide patient transfer and patient thermal control simultaneously.

As described above, patients may be transferred between a variety of surfaces or structures in a healthcare facility. Logistics of patient transfers are becoming more difficult due at least in part to fewer healthcare workers to perform the transfers, the increasing average weight of patients, and the increasing average age of healthcare workers. While many hospitals have instituted "no lift" policies, sliding patients can be difficult or painful for workers and can cause pain or discomfort to the patient as well.

Many patient transfers in a healthcare setting include what are referred to as "flat" transfers, where the patient is transferred from one flat surface to another, and where both surfaces are at close to the same height. A variety of objects and devices have been used to assist with such flat transfers, including plastic garbage bags, roller boards, air-assisted mattresses, and the like.

The air-assisted mattresses generally include holes in the bottom surface. The patient is rolled over and the deflated mattress is placed under the patient. The mattress is then inflated (e.g., using the pressure side of a HEPA filtered vacuum cleaner, etc.). When the mattress is fully inflated, the air escapes out the holes in the bottom, essentially putting the patient on an air pallet. Such air-assisted mattresses can include several drawbacks, including at least the following:

i. "Ballooning" and/or "Hot dogging"—the mattresses can bloat during inflation, such that the load becomes unbalanced on the mattress's footprint. The thin, flexible fabric of the mattress can tend to become hemispherical, in the sense that when one area is indented (e.g., by the weight of the patient), another remote area can bulge, which can create an unstable situation in which the patient can be dislodged. To inhibit ballooning or hot dogging, some devices include extensive internal sheets that are sewn to the top and bottom faces of the mattress. These internal sheets can restrict ballooning but also add greatly to the cost of the device since they must be individually sewn.
  ii. Time Consuming and Multi-step—the mattresses generally need to be fully inflated (e.g., to ensure sufficient rigidity and air pressure of the air pallet), while the patient is buckled in, to a height of about 6-10 inches (15-25 cm). Inflating the mattress can be time-consuming and noisy and the patient transfer is put on hold to wait for the mattress to become inflated.
  iii. Disinfection—the mattress fabric is generally a durable knit or woven fabric type construction having an occlusive film on the interior surface to form an hermetic seal. The relatively high cost of the air-assisted mattresses leads to their reuse. The fabric pores create a surface that is difficult to disinfect, and identifying a device that has been disinfected can be difficult, if not impossible. In addition, contaminant particles and microorganisms (virus, bacteria, spores) can penetrate into the mattress material and when the mattress is inflated, the pressure can force the particles out and into the air.
  iv. High maintenance—in many cases, the clinicians need to track the limited number of expensive air-assisted mattresses in the hospital, and the mattresses are often misplaced.
  v. Bulky—the mattresses are generally formed of heavy duty fabric for durability, generally causing the mattresses to be heavy and bulky devices that are difficult to store and efficiently transport.

In contrast, the systems and methods of the present disclosure are generally directed to three-dimensional, non-inflatable platforms that define a plenum that can be filled with a fluid (e.g., liquids, gases, or combinations thereof), and which can move the fluid into the plenum and out a plurality of apertures that are positioned to create a fluid pallet (e.g., an air pallet) underneath a patient and/or to convectively warm or cool a patient positioned atop the platform. Unlike air-assisted mattresses, time need not be wasted waiting for the non-inflatable platforms to sufficiently fill. In addition, the non-inflatable platforms can be self-supporting and/or non-collapsible and can avoid "ballooning" or "hot-dogging." Some or all of the surfaces of the non-inflatable platforms of the present disclosure can be smooth and easy to clean and disinfect. The non-inflatable platforms of the present disclosure can be designed for low-cost, efficient manufacturing and can be low enough cost that they can truly function as a disposable patient pallet. In some embodiments, the patient can be placed on the platform or pallet of the present disclosure and moved throughout the hospital without leaving, or rarely leaving, the pallet.

In general, the platform can include a first surface and a second surface that is positioned substantially parallel to the first surface and separated by a gap from the first surface by a separation layer. The separation layer can be formed by or include a plurality of supporting structures, which can extend from one surface toward the other (or both), and which can optionally extend along a major surface of one or both of the surfaces forming the platform. The separation layer can serve at least two functions: (i) the separation layer can maintain separation between the top (first) and bottom (second) surfaces even when under load such as when a patient is lying upon the top surface; and (ii) the separation layer can serve as a fluid conduit forming a plenum in conjunction with the first and second surfaces to move pressurized fluid from a fluid source (e.g. a blower) to the outlet apertures. The plurality of supporting structures can function to maintain the separation of the first and second surface, and can at least partially define the plenum, or a series of individual plenums (e.g., channels), that can be fluidly coupled to a positive pressure fluid source to move fluid into the plenum(s) and out the plurality of apertures (i.e., for patient transfer and/or thermal control). That is, the fluid may be moved in the platform along a series of channels or ducts that can be at least partially defined by the plurality of supporting structures, and/or it may be moved in a single chamber (i.e., plenum) around and/or through the plurality of supporting structures. Various embodiments of the patient support systems and methods of the present disclosure are described in greater detail below with reference to the figures. The systems and methods of the present disclosure can be useful in a variety of patient care applications, including, but not limited to, patient transfers, acute and chronic active patient warming or cooling, pressure ulcers reduction in acute and long-term care patients, management of urine and other fluids, and combinations thereof.

By way of example only, pressure ulcers can be inhibited from occurring by providing fluid flow (e.g. airflow) beneath a patient to maintain healthy skin integrity during his/her stay. Warm or cold air, for example, may be circulated under the patient which may further be humidity controlled. For example, moist skin can be significantly more susceptible to damage due to pressure and/or shear and thus it may be beneficial to circulate a relatively dry fluid (e.g. air having a relative humidity of less than 50% and, in some embodiments, less than 30%) beneath the patient. In addition, additional accessories, such as conformable and/or inflatable cushions, can be positioned as desired under the patient, such as under a patient's heels. In embodiments in which the cushions are inflatable, the cushions can be fluidly coupled to the same fluid source as the plenum described above, such that the cushions are inflated as the plenum is pressurized.

As a result, the systems and methods of the present disclosure can be used in a variety of applications. Furthermore, some embodiments of the systems and methods of the present disclosure can provide at least some of the following features:

i. Disposable—the platform can stay with a given patient throughout his/her stay in the healthcare facility and can then be disposed, and therefore, there is no need to track the device;

ii. Disinfectable—the platform can be formed of a non-absorbent, easy to clean (e.g., non-porous) material, such that the surfaces presented to the environment need not be disinfected or are easily disinfected or wiped clean;

iii. Non-inflatable—no need to wait for the platform to inflate in order to move fluid out the plurality of apertures;

iv. Increases worker safety in patient transfer applications;

v. In patient thermal control applications, the platform can warm or cool the patient from underneath, leaving the clinicians free access to the patient;

vi. The platform of the device is positioned underneath a patient and the patient is inhibited from slipping off of the platform, such as is possible with inflatable support systems; and combinations thereof.

FIG. 1 illustrates a patient support system 100 according to one embodiment of the present disclosure. The patient support system 100 includes a platform 102 mechanically coupled and fluidly coupled to a fluid source 104 optionally via a connector 106 (e.g., a hose) and/or a manifold 108. The fluid source 104 can be configured to provide fluid under positive pressure to the platform 102, for example, for patient transfer and/or patient warming/cooling applications. The connector 106 and manifold 108, are shown by way of example only, and it should be understood that the platform 102 can be positioned in fluid communication with the fluid source 104 by a variety of suitable means.

The fluid source 104 can include any suitable fluid source capable of providing fluid under a positive pressure to the platform 102, such as a pump or blower, a pressure side of a HEPA vacuum cleaner, other suitable fluid sources, or combinations thereof. In some embodiments, the fluid source 104 can be capable of delivering fluid at a sufficient volume and pressure to significantly reduce the force necessary to transfer a patient even over porous surfaces such as bed linens. In some embodiments, the fluid source 104 can deliver a pressure of (and the platform 102 can withstand an internal pressure of) at least about 3 kPa, in some embodiments, at least about 5 kPa, in some embodiments, at least about 10 kPa, in some embodiments, at least about 15 kPa, in some embodiments, at least about 20 kPa, and in some embodiments, at least about 35 kPa. In some embodiments, the fluid source 104 can be capable of delivering fluid at a volumetric flow rate of at least about 500 $L^3$/min., in some embodiments, at least about 1000 $L^3$/min., in some embodiments, at least about 1500 $L^3$/min, and in some embodiments, at least about 2000 $L^3$/min. In addition, the patient support system 100 can be configured to run on alternating current, direct current or battery, or a combination thereof.

In some embodiments, the fluid source 104 can include an air filter to remove contaminants, such as dust, debris, bacteria, viruses, etc. In some embodiments, such filters could be placed at the inlet of the fluid source 104 or at the inlet 129 of the manifold 108, or in both locations. In some embodiments, the internal surfaces defining a plenum 120 (described below) in the platform 102 and/or the manifold 108 may also be at least partially filled with a suitable filtration material and/or or electrostatically charged to capture dust and microbes, etc.

In some embodiments, the fluid source 104 can include or be coupled to a heat transfer (or thermal control) unit, such that fluid provided in the platform 102 can be heated or cooled, as desired, for example, for patient thermal control. Examples of such embodiments are described in greater detail below, for example, with respect to FIG. 5.

As shown in FIG. 1, in some embodiments, the patient support system 100 can include a plurality of platforms or platform segments 102 that can be coupled together to form a desired size and/or shape for a particular application. An outline of a second platform 102A is shown in dashed lines in FIG. 1. In such embodiments, each platform 102 can each independently be fluidly coupled to the fluid source 104, each platform 102 can be fluidly coupled to an individual fluid source 104, the platforms 102 can be in fluid communication with each other and the fluid source 104, or a combination thereof. Platform segments 102 may be configured to allow easy folding and/or rolling of the platform segments 102 one over another for convenient packaging and storage. For example, as shown in FIG. 1, in some embodiments, the patient support system 100 can include one or more connecting sections 103 positioned to couple (e.g., mechanically and/or fluidly) one or more platform segments 102. Such connecting sections 103 can be inflatable or non-inflatable, and can be flexible to facilitate folding and/or stacking the platform segments 102 (e.g., particularly if rigid platform segments 102 are employed). The connecting sections 103 can be solid or hollow. If hollow, the connecting section 103 can be in fluid communication with one or more plenum(s) 120 of one or more platform segments 102.

In some embodiments, the platform 102 can be formed of a plurality of smaller, relatively rigid segments that are separated from one another by flexible connecting sections 103, such that the platform 102 as a whole may have a somewhat flexible nature, even though the platform segments or panels are relatively rigid. In such embodiments, the segments or panels can be easily coupled to one another and/or decoupled from one another to create a modular platform 102 that can easily be made to a desired shape and size, for example, to accommodate a particular patient size. Whether the platform 102 is formed of one portion or segment or a plurality of portions, in some embodiments, the platform 102 can include an overall length of about 8 ft (2.4 m) and an overall width of about 4 ft (1.2 m).

As further shown in FIG. 1, the platform 102 can include a first (top) sheet or surface 110 and a second (bottom) sheet or surface 112 positioned substantially parallel to the first surface 110 and separated from the first surface 110 by a distance d. As a result, each of the first surface 110 and the second surface 112 can define a major surface that extends in the direction of its length and width and which faces the major surface of the other surface. While a constant distance d is shown for simplicity in FIG. 1, it should be understood that the distance d can change throughout the platform 102 and need not be a constant or fixed distance d over the entire platform 102.

In some embodiments, the platform 102 can be large and strong enough to support at least the torso section of a patient, can be thin and low-profile, can have a relatively high tensile and/or bending strength, and can be configured to be pressurized to provide fluid flow out from apertures 122 (and/or out any additional apertures, for example, to provide patient warming and/or cooling). The apertures 122 can have any configuration, including defining a straight through-hole, being oriented at an angle, defining a non-linear path, having a length as well as a depth and therefore defining a slit, other suitable configurations, or combinations thereof.

Regarding thickness or profile of the platform 102, in some embodiments, the platform 102 can have a thickness of less than about 1 inch (about 2.5 cm), in some embodiments, less than about 0.5 inches (about 1.3 cm), in some embodiments, less than about 0.25 inches (about 0.6 cm), and in some embodiments, less than about 0.125 inches (about 0.3 cm).

In some embodiments, the platform 102, or a portion thereof, can be radiotranslucent so as not to interfere with X-ray diagnostic procedures. In other embodiments, the platform 102 can be free of materials which may interfere with or be attracted to the magnet of a magnetic resonance imaging (MRI) instrument. Furthermore, in some embodiments, the platform 102 is not coupled or adhered to a patient during use, which can avoid skin compromise on a patient.

The platform 102, or a portion thereof (e.g., the first surface 110 and the second surface 112), can be formed of a variety of materials, such as composite materials, polymeric materials (e.g., thermoplastic, thermoset, biodegradable, or combinations thereof), or combinations thereof. In some embodiments, the platform 102, or a portion thereof (e.g., the first surface 110 and the second surface 112), can be formed of a non-absorbent, microporous, and/or nonporous material that is resistant to harboring bacteria and other soil. As a result, the platform 102, or the respective portion thereof, can be easily cleaned and/or disinfected. In addition, in some embodiments, the platform 102, or a portion thereof (e.g., the first surface 110 and the second surface 112), can include an antimicrobial layer or coating to inhibit microbes from collecting and/or growing on the platform 102. In some embodiments, the platform 102 can be formed of materials that are compatible with common disinfectants and cleaners, such as oxidizers (e.g., bleach, hydrogen peroxide, dilute peracetic acid, and the like), quaternary ammonium disinfectants (e.g. dimethyldidecylammonium bromide), phenolic compounds (e.g. triclosan), cleaning surfactants (e.g. sodium dodecyl sulfate), as well as solvents (e.g. glycol ethers such as hexyl Cellosolve or hexylCarbitol).

Examples of thermoplastic materials can include one or more of polyolefins (e.g., polyethylene (high density polyethylene (HDPE), low density polyethylene (LDPE), linear low density polyethylene (LLDPE), metallocene polyethylene, and the like, and combinations thereof), polypropylene (e.g., atactic and syndiotactic polypropylene)), polyamides (e.g. nylon), polyurethane, polyacetal (such as Delrin), polyacrylates, and polyesters (such as polyethylene terephthalate (PET), polyethylene terephthalate glycol (PETG), and aliphatic polyesters such as polylactic acid), fluoroplastics (such as THV from 3M company, St. Paul, Minn.), and combinations thereof.

Examples of thermoset materials can include one or more of polyurethanes, silicones, epoxies, melamine, phenol-formaldehyde resin, and combinations thereof.

Examples of biodegradable polymers can include one or more of polylactic acid (PLA), polyglycolic acid (PGA), poly(caprolactone), copolymers of lactide and glycolide, poly(ethylene succinate), polyhydroxybutyrate, and combinations thereof.

In embodiments employing a polymeric platform 102, the platform 102 can be formed by a variety of methods, including relatively facile manufacturing methods, such as extrusion, molding, or combinations thereof.

In some embodiments, one or more surfaces of the platform 102 (e.g., a major surface of the first surface 110 and/or the second surface 112), or a portion thereof, can include a low friction surface, which can be achieved by the material composition and texture of the respective surface or by treating the surface (e.g., with a coating, by coupling a low-friction layer to a desired portion of the platform 102, etc.). A "low friction" surface can generally be used to refer to a surface having a low kinetic coefficient of friction. In some embodiments, a low friction surface can include a kinetic coefficient of friction of no greater than about 1, in some embodiments, no greater than about 0.5, and in some embodiments, no greater than about 0.25, when measured on a flat film, sliding against another piece of the same material in accordance with ASTM D1894-08 Static and Kinetic Coefficients of Friction of Plastic Film and Sheeting. The first surface 110 and the second surface 112 can be formed of the same or different materials, such that desired portions of the platform 102 have desired levels of rigidity and flexibility.

The term "flexible" can generally be used to refer to a material that is drapable. That is, a section of material 5 cm×15 cm when held upright (long end up) folds over under its own weight to drop the opposite end to or below the holder, when performed at ambient conditions. The term "rigid" can generally be used to refer to a material that is essentially non-drapable. That is, a section of material 5 cm×15 cm when held upright (long end up) stands straight up with little or no deflection, when performed at ambient conditions. In some embodiments, rigid materials can show less than 20 degrees of deflection from vertical. "Semi-rigid" materials can be those that exhibit more than 20 degrees of deflection but whose opposite end does not drop below the holder.

In some embodiments, the entire platform 102 is formed of flexible material (or combination of flexible materials), and in some embodiments, the entire platform 102 is formed of a rigid material (or combination of rigid materials). However, in some embodiments, the first surface 110, or a portion thereof, can be formed of a flexible material, and the second surface 112, or a portion thereof, can be formed of a rigid material, or vice versa. For example, in some embodiments, the first surface 110 or the second surface 112 is formed entirely of a rigid material, while a portion of the other surface 112 or 110 is formed of a rigid material, and the remaining portion of the other surface 112 or 110 is formed of a flexible material. By way of further example, the first surface 110 or the second surface 112 can be formed entirely of a flexible material, while a portion of the other surface 112 or 110 is formed of a flexible material, and the remaining portion of the other surface 112 or 110 is formed of a rigid material. As such, various combinations are possible and can be contemplated.

The platform 102 can be relatively thin and easily transportable along with a patient throughout his/her stay or procedure. However, in some embodiments, the platform 102 can also have a sufficient strength to bridge gaps that may exist between two transfer surfaces, for example, in a patient transfer application. In some embodiments, the platform 102 can be relatively stiff and have a bending strength (e.g., a three-point bending strength) of at least about 5 N, in some embodiments, at least about 10 N, and in some embodiments, at least about 20 N in at least one major axis in a non-pressurized state. "Bending strength" as used herein is determined in accordance with Example 1 and ASTM D 790-07 Procedure B when performed in both the major axes of one embodiment of a platform of the present disclosure, which was cut to a width of 20 mm and a length of 100 mm, for the purpose of testing.

In some embodiments, the platform 102 can be relatively flexible, which can afford facile storage and transportation of the platform 102, such as by rolling or folding. In such embodiments, the bending strength of the platform 102 may be no greater than about 5 N, and in some embodiments, no greater than about 2 N. In some embodiments, the platform 102 may be so flexible that, when cut to a width of 20 mm and a length of 100 mm, it cannot span the supports to determine a bending strength in at least one major axis in a non-pressurized state. Platforms 102 that are relatively flexible in a non-pressurized state can be sufficiently rigid or stiff in a pressurized state. For example, some platforms 102 that are flexible when they are not pressurized can include the bending strengths described above with respect to relatively rigid platforms 102 when they are pressurized. As such, the relatively flexible non-pressurized platforms 102 can be sufficiently rigid in their pressurized state, e.g., to support a patient.

Whether the platform 102 is rigid, flexible, or a combination thereof, the platform 102 can be a three-dimensional and non-inflatable structure. The term "non-inflatable" can generally be used to refer to an object that exhibits a uni-dimensional change in size (e.g., length, height) or a three-dimensional change in size (e.g., volume) of no greater than 200%, in response to an increase in internal pressure in use, compared to the nonpressurized state. In some embodiments, "non-inflatable" can refer to an object that changes uni-dimensionally or three-dimensionally by no more than 100%, in some embodiments, no more than 50%, in some embodiments, no more than 30%, and in some embodiments, no more than 10% in response to an increase in internal pressure, compared to the nonpressurized state. In some embodiments, the platform 102 has a nondetectable change in size (e.g., uni-dimensional and/or three-dimensional).

For the purpose of testing percent increase in size, the dimensions can be measured with an internal pressure in the plenum of about 1.5 psig (about 10.5 kPa). To facilitate testing, 15 cm×15 cm sections of the platform 102 may be formed (e.g., cut out) to estimate the initial relaxed, nonpressurized size (e.g., uni-dimensional and/or three-dimensional).

In addition, the platform 102 can be self-supporting. The term "self-supporting" can generally be used to refer to an object that does not collapse under its own weight under ambient conditions. For example, in some embodiments, the term "self-supporting" can generally refer to a platform in which a gap is maintained between the first surface and the second surface under ambient conditions (i.e., where there is no positive pressure provided to the plenum; 0 psig, 0 Pa). Said another way, the term "self-supporting" can generally refer to a platform in which the first surface and the second surface do not come into contact with one another under ambient conditions. "Ambient conditions" can generally refer to room temperature (e.g., about 25° C.) and atmospheric pressure (e.g., gauge pressure of zero).

Furthermore, in some embodiments, the platform 102 can be non-collapsible. The term "non-collapsible" can generally be used to refer to an object that does not collapse in response to an externally applied pressure of up to and including a threshold pressure or load. In some embodiments, the threshold pressure or load can be about 700 Pa, in some embodiments, about 3 kPa, in some embodiments, about 5 kPa, in some embodiments, about 10 kPa, in some embodiments, about 15 kPa, in some embodiments, in some embodiments, about 20 kPa, in some embodiments, about 40 kPa, and in some embodiments, about 50 kPa. Measurement of whether a platform is collapsible can be made at the center of the load portion(s) and can be accomplished by taking a stiff metal plate of known weight and area (e.g. 7.5 cm square) and adding weight(s) on top of the plate until the first and second surfaces "collapse" and touch one another. The measurement can be taken once on each sample since repeat measurements on the same section would likely result in lower values. The "threshold" pressure can be taken as the externally applied pressure where any portion of the top and bottom surfaces in the section under load touch.

For example, in some embodiments, the term "non-collapsible" can generally refer to a platform in which a gap is maintained between the first surface and the second surface in response to an external pressure of no greater than the threshold pressure. Said another way, the term "non-collapsible" can generally refer to a platform in which the first surface and the second surface do not come into contact with one another in response to an externally applied pressure of no greater than the threshold pressure. As described in greater detail below, maintenance of the gap between the first and second surfaces can be at least partially accomplished by employing supporting structures that extend at least partially across the distance between the first and second surfaces. In some embodiments, the platform 102 (e.g., including such supporting structures) can support a pressure or load of at least about 35 kPa, in some embodiments, a load of at least about 50 kPa, and in some embodiments, a load of at least about 75 kPa, without collapsing.

In some embodiments, depending on the material makeup and/or structure of the platform 102 (e.g., as a result of the non-inflatable, self-supporting nature of the platform 102), the platform 102 can withstand significant internal pressures (e.g., those listed above as being provided by the fluid source 104) without bursting, cracking or breaking, which can allow the platform 102 to support relatively large patients (e.g., morbidly obese patients, such as patients weighing more than 350 lbs (about 160 kg). In patient transfer applications, this can allow the platform 102 to lift and move large patients. This can be a significant advantage over inflatable mattress systems, in which the mattress can only withstand relatively low internal pressures, such as less than 10 kPa or 15 kPa.

In some embodiments, employing a non-inflatable, self-supporting platform 102 can avoid some of the issues identified above associated with inflatable devices, such as the time-consuming and noisy inflation process; ballooning and hot dogging and the potential roll-off dangers associated with these characteristics; and the storage and transportation of large bulky objects that are designed to be reused.

In some embodiments, the platform 102 can be non-inflatable, self-supporting and/or non-collapsible as a result of the material makeup and/or construction of the platform 102. In some embodiments, as shown in cut-away portion of FIG. 1, the patient support system 100 can further include one or more supporting structures 114 that can extend at least partially across the distance d or gap between the first surface 110 and the second surface 112. In such embodiments, the supporting structures 114 can be at least partially responsible for the platform 102 being self-supporting and/or non-collapsible, and at least some of the supporting structures 114 can include a component that extends substantially orthogonally with respect to the major surfaces of the first surface 110 and/or the second surface 112.

The supporting structures 114 can be optionally coupled to one or both of the first surface 110 and the second surface 112. In some embodiments, at least some of the supporting structures 114 can be integrally formed with one or both of the first surface 110 and the second surface 110. For example, in some embodiments, the platform 102, or a portion thereof, can be extruded and/or molded to form supporting structures 114 integrally formed with one or both of the first surface 110 and the second surface 112. In some embodiments, the first surface 110, the second surface 112 and the supporting structures 114 form a unitary and integral structure (see, e.g., FIGS. 3, 4 and 11-13 and their accompanying descriptions below).

Furthermore, it should be understood that the first surface 110 and/or the second surface 112 can alternatively be separate sheets of material which are not integrally formed with supporting structures 114. That is, the first surface 110, the second surface 112 and/or the supporting structures 114 can be formed of different materials from one another. In some embodiments, the first surface 110 and/or the second surface 112 can be in the form of a sheet, and may not be integrally formed with the supporting structures 114. Rather, in such embodiments, the first surface 110 and/or the second surface 112 can be joined, bonded, affixed or otherwise coupled to the supporting structures 114 by any number of means know to one skilled in the art, including but not limited to, adhesive bonding, melt bonding or a suitable mechanical fastening.

Thus, in some embodiments, the term "sheet" can be used interchangeably with the term "surface." In some embodiments, the platform 102 can be constructed with the first surface 110 and the second surface 112 in the form of sheets (e.g., either one large tubular sheet forming the first surface 110 and the second surface 112, or two separate sheets). In such embodiments, the supporting structures 114 can be positioned between the first surface 110 and second surface 112, with the supporting structures 114 not being bonded or otherwise coupled in any manner to the sheet(s) forming the first surface 110 and the second surface 112. For example, such supporting structures 114 can include posts, rails, solid tubes, hollow tubes, walls, partial walls, or other suitable structures that extend at least partially across the distance between the first surface 110 and the second surface 112, that inhibit the platform 102 from collapsing, and that at least partially define one or more plenums 120 in the platform 102. In some embodiments, the supporting structures 114 are coupled to (e.g., by being chemically or mechanically affixed to and/or by being integrally formed with) one or both of the first surface 110 and the second surface 112. Whether or not the supporting structures 114 are coupled to the first surface 110 and/or the second surface 112, the supporting structures 114 generally define an "open" network of one or more channels or fluid pathways that facilitates fluid movement therethrough.

At least portions of the first and second surface 110 and 112 can be optionally coupled together (e.g., at least partially via the supporting structures 114), but the first and second surfaces 110 and 112 maintain the distance d between them, to provide a chamber or plenum 120 therebetween. The plenum 120 is at least partially defined by the first surface 110, the second surface 112, and the plurality of supporting structures 114. The plenum 120 is fluidly coupled to the fluid source 104 via the connector 106 and the manifold 108. By way of example only, in the embodiment illustrated in FIG. 1, each supporting structure 114 includes a z-dimension that generally extends along a z-direction between the first surface 110 and the second surface 112 and assists in maintaining the distance d between the first surface 110 and the second surface 112. In addition, each supporting structure 114 in FIG. 1 also includes an x-dimension (or a y-dimension) oriented substantially orthogonally to the z-dimension that extends along (or substantially parallel to) a major surface of one or both of the first and second surfaces 110 and 112 along an x- or a y-direction.

It should be noted, however, that the supporting structures 114 need not have the shape shown in FIG. 1. Rather, the supporting structures 114 can have a variety of shapes (including three-dimensional or cross-sectional shapes), including but not limited to, cylindrical, pyramidal, rectangular, triangular, and hook-shaped (see, e.g., FIGS. 6B-10 and their accompanying descriptions below), parallelepipedal, spherical, hemi-spherical, polygonal, conical, frusto-conical, other suitable shapes, and combinations thereof. It should be further noted that the supporting structures 114 can be in the form of (i) rails or walls that include a z-dimension as well as an x- and/or y-dimension (i.e., extend in a z-direction as well as an x- and/or y-direction), (ii) posts, pegs or pins that primarily include a z-dimension (i.e., that primarily extend between the first surface 110 and the second surface 112), and (iii) combinations thereof. Such posts or pegs can further include a cap, shroud, extension, or the like, as will be described in greater detail below with reference to FIGS. 6B-10.

In addition, the supporting structures 114 can be arranged in any desired configuration, as described in greater detail below. The supporting structures 114 can be formed of any of the materials described above with respect to the platform 102, as the supporting structures 114 generally form a portion of the platform 102. The supporting structures 114 can be formed to include a desired strength under compression to support a desired load or pressure.

In addition, as shown in FIG. 1, in some embodiments, a plurality of apertures 122 can be formed through at least a portion of the second surface 112, such that the apertures 122 are in fluid communication with the plenum 120 to allow fluid to exit the plenum via the apertures 122. By way of example only, the patient support system 100 illustrated in FIG. 1 is configured for a patient transfer application, such that the apertures 122 are formed only through the second surface 112, which is adapted to face away from a patient during use, and not the first surface 110, which is adapted to face a patient during use. However, as described in greater detail below, in some embodiments, the patient support system can be configured for patient transfer, patient warming or cooling, a combination thereof, and/or other applications. In such embodiments, additional apertures can be formed through the first surface 110 in addition to or in lieu of the apertures 122 formed through the second surface 112.

In some embodiments, the apertures 122 can be open at all times (e.g., perforations), and in some embodiments, at least some of the apertures 122 can include or be coupled to one-way valves (e.g., one-way pressure-activated valves) that can be configured to open only when a threshold pressure within the plenum 120, or a portion thereof, has been reached. Such valves can include, but are not limited to, a variety of manual or automatic valves, an electronic pressure transducer, check valves (e.g., duckbill valves, ball check valves, diaphragm check valves, swing check valves, stop check valves, lift check valves, reed valves, etc.) or other types of valves, such as stopcock valves, butterfly valves, metering valves, constant volume metering valves, timer valves, tapered valves (e.g., where the aperture 122 tapers from the plenum side to the external side of the first surface 110 or the second surface 112), other suitable valves, or combinations thereof. In some embodiments, a combination of open apertures 122 and valved apertures 122 can be employed.

Figure 3:
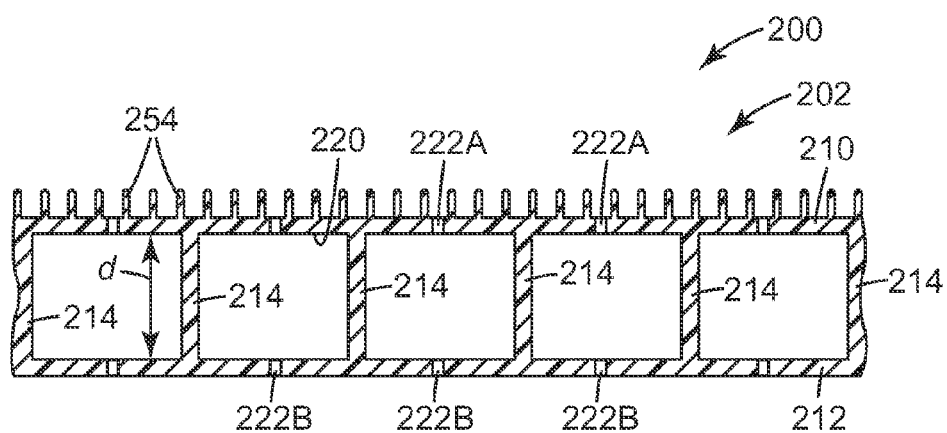
FIG. 3 is a cross-sectional view of the patient support system of FIG. 2, taken along line 3-3 in FIG. 2.

In some embodiments, as shown in FIG. 3, the apertures 222 can be substantially straight and can be oriented substantially orthogonally with respect to a major surface of the first surface 210 and/or the second surface 212. Such a configuration can be useful for patient transfer applications, in which fluid can efficiently and reliably exit the apertures 222 toward another surface or structure, such as a bed or table, to provide a sufficient fluid pallet. However, it should be understood that other aperture configurations and orientations can be employed, for example, to direct the fluid exiting the apertures 222 as desired. In addition, in some embodiments, the apertures 222 may not take a straight path through the first surface 210 and/or second surface 212.

The apertures 122 of the present disclosure (e.g., apertures 122 of FIG. 1 or apertures 222 of FIG. 3) can be arranged in a variety of arrangements, including regular patterns or arrays, or irregular or random arrangements. In some embodiments, the apertures 122 can be very small holes or perforations. Furthermore, the apertures 122 have a variety of cross-sectional shapes (e.g., when sectioned along a plane that is substantially perpendicular to the first and second surfaces 110 and 112), including but not limited to, circular, square, rectangular, triangular, polygonal, other suitable shapes, and combinations thereof. By way of example only, in some embodiments, the apertures 122 can have a substantially circular cross-sectional shape and a diameter of approximately 0.070 inches (0.18 cm), and the apertures 122 can be arranged in a grid arrangement, with the apertures 122 placed approximately every square inch (approximately every 6.5 square centimeters). However, aperture size, shape and arrangement can be determined based on the desired application. By way of example only, in some embodiments, the apertures 122 can be formed in the first surface 110 and/or the second surface 112 by means of the extrusion process or by a secondary process, such as one that forms hot or cold needle perforations in the surfaces.

In addition, in some embodiments, as shown in FIG. 1, the platform 102 (or the first or second surface 110 or 112) can include a first portion 126 in which the apertures 122 are formed and a second portion 128 in which the apertures 122 are not formed. As a result, the apertures 122 need not be formed entirely over a major surface of the first surface 110 or the second surface 112. Rather, the apertures 122 can be formed wherever necessary for a given application.

In some embodiments, the first portion 126 can be positioned outwardly of the second portion, relative to a center of the platform 102. For example, in such embodiments, the apertures 122 can be formed toward a periphery of the platform 102, while the center of the platform 102 can be substantially free of apertures 122. This could be the case, for example, in embodiments employing patient thermal control in which the first surface 110 includes apertures formed through a first portion but not a second portion. Such apertures could be employed instead of or in addition to the apertures 122 shown formed through the second surface 112 of the patient support system 100.

In some embodiments, as shown in FIG. 1, the second portion 128 of the platform 102 can be positioned outwardly of the first portion 126, or toward a periphery of the platform 102, such that the second portion 128 includes an outer peripheral area where no apertures are formed. Such a configuration can be used, as shown in FIG. 1, in embodiments employing patient transfer, to focus the fluid pallet to a desired region of the platform 102.

In some embodiments, the platform 102 can include multiple first portions 126 comprising apertures 122 and/or multiple second portions 128 comprising no apertures, and the multiple first portions 126 and/or second portions 128 can be arranged as desired for a particular use.

In some embodiments, as mentioned above, the first surface 110 can include additional apertures (e.g., see FIG. 2), that are adapted to be used, for example, for patient thermal control, in addition to the apertures 122 that can be used for patient transfer. In such embodiments, the second surface 112 may include a first portion 126 and a second portion 128 as shown in FIG. 1, and the first surface 110 may further include one or more first portions and/or second portions positioned and arranged to achieve a desired function, such as patient thermal control. The first portion(s) on the first surface 110 need not correspond to the first portion(s) 126 on the second surface 112. For example, in some embodiments, the first surface 110 can include a first portion comprising apertures that is positioned toward a periphery of the first surface 110, relative to a second portion that does not include apertures. Such apertures can be positioned, for example, to deliver a heated (e.g., to a temperature of about 35-42° C.) fluid (e.g., warmed air) to a patient positioned adjacent the first surface 110. The second surface 112 of such embodiments can additionally include the first portion 126 comprising the apertures 122 and the second portion 128 that does not include the apertures 122, as shown in FIG. 1. In such embodiments, the apertures formed in the first surface 110 can be positioned toward a periphery of the platform 102, while the apertures 122 formed in the second surface 112 are formed toward the center of the platform 102.

As mentioned above, the supporting structures 114 can have any desired configuration that allows the plenum 120 to fluidly communicate with both the fluid source 104 and the apertures 122. In the embodiment shown in FIG. 1, the supporting structures 114 form walls that divide the plenum 120 into a plurality of plenums 120 (e.g., fluid channels) that are each fluidly coupled to the manifold 108 and in fluid communication with the fluid source 104. However, it should be understood that each supporting structure 114 need not extend along the length of the first and second surfaces 110 and 112, and the plurality of plenums 120 need not be entirely discrete from another. In some embodiments, the supporting structures can be much shorter and even in the form of posts, pegs, pins, or the like, such that the space between the first and second surfaces 110 and 112 defines one plenum 120. In such cases, the supporting structures 114 need not be arranged in a regular array or pattern, but rather can be irregular or arranged in regions. Still, in some embodiments, a combination of smaller discrete plenums (e.g., channels, pockets, chambers) and larger plenums can be employed. Such configurations can be achieved, for example, when a combination of post-like and rail-like supporting structures 114 are employed.

While shown as flat, planar sheets in FIG. 1, the first and second surfaces 110 and 112 need not be planar. Rather, the first and second surfaces 110 and 112 may have a variety of cross-sectional shapes. For example, one or both of the first surface 110 and the second surface 112 may have dimples or depressions (e.g., concave or convex domes), or a variety of other shapes. In some embodiments, such depressions may form an attachment means for the supporting structures 114 and/or they may comprise one or more apertures 122 (e.g., see FIGS. 12 and 13 and the accompanying description). In some embodiments, one or both of the first surface 110 and the second surface 112 can have a variety of other cross-sectional shapes, such as a sinusoidal cross-sectional shape.

Furthermore, in some embodiments, the supporting structures 114 are all the same size, as shown in FIG. 1. However, in some embodiments, a variety of supporting structures 114, of varying shapes and/or sizes (e.g., heights), can be employed.

One example of a material that can be used as at least a portion of the platform 102 of the patient support system 100, including the supporting structures 114, is a CORRUBOARD twin walled hollow profile plastic sheets (available from Corplast Packaging Industry, Malaysia; see www.corplast.com).

In some embodiments, the patient support system 100 includes one or more fluid paths 125 that can be at least partially defined by one or more inlets 127 into the plenum(s) 120, the plenum(s) 120, and the apertures 122. In some embodiments, the one or more fluid paths 125 can be defined by the fluid source 104, optionally the connector 106 and/or the manifold 108, optionally the one or more inlets 127, the plenum(s) 120, and the apertures 122.

In some embodiments, the fluid pressure at the inlet(s) 127 to the plenum(s) 120 (which can be measured at an inlet 129 to the manifold 108 or at an inlet 127 to a plenum 120) can be at least about 3 kPa, in some embodiments, at least about 5 kPa, in some embodiments, at least about 10 kPa, and in some embodiments, at least about 15 kPa. In some embodiments, the fluid pressure at the inlet(s) 127 to the plenum(s) 120 can be no greater than about 40 kPa, in some embodiments, no greater than about 35 kPa, and in some embodiments, no greater than about 20 kPa.

The inlet 129 to the manifold 108 is shown as being at one end of the manifold 108; however, it should be noted that the inlet 129 can be positioned at any point along the length of the manifold 108, or at multiple locations along the length of the manifold 108 (e.g., by employing a Y hose (and, optionally, additional connectors) between the connector 106 and the manifold 108, or the like.

As shown in FIG. 1, in some embodiments, the patient support system 100 can further include a skirt 130 (otherwise sometimes referred to as a "fluid skirt," an "apron," a "seal," a "baffle," or the like) that can be used to direct fluid exiting the apertures 122. For example, as shown in FIG. 1, the skirt 130 can be coupled to the second surface 112 (and/or the first surface 110 if additional apertures are formed in the first surface 110), and positioned between the first portion 126 in which the apertures 122 are formed and the second portion 128 in which no apertures are formed to inhibit fluid flowing out of the apertures 122 from escaping to the sides of the platform 102, e.g., in a direction substantially parallel to the second surface 112. Said another way, the patient support system 100 can include a skirt 130 that is positioned adjacent the apertures 122 to assist in directing the fluid exiting the apertures 122 as desired (e.g., to inhibit fluid from exiting the apertures 122 in a direction substantially parallel to one or both of the first surface 110 and the second surface 112). The apron or skirt 130 can serve to contain the fluid and facilitate lifting the platform 102 from a supporting surface, thus decreasing the force needed to move the loaded platform 102. The skirt 130 can be particularly useful in patient transfer applications to assist in creating a sufficient fluid pallet and generating sufficient force under the platform 102 to lift the platform 102 and a patient and to allow the platform 102 and patient to be moved. However, the skirt 130 may also be employed in other uses or applications.

The skirt 130 is shown in FIG. 1 by way of example as including a portion that is positioned between the first portion 126 and the second portion 128 of the platform 102. However, the skirt 130 can be positioned as necessary to assist in directing the fluid exiting the apertures 122. In some embodiments, the skirt 130 can be positioned adjacent an outer edge (or along a periphery) of the platform 102 (or the first and/or second surface 110 and/or 112). In addition, in some embodiments, as shown in FIG. 1, the skirt 130 can include a grid pattern. As such, the skirt 130 of FIG. 1 includes a plurality of sections oriented along the width of the platform 102 and a plurality of sections oriented along the length of the platform 102 that intersect to form a plurality of individual cells of a fluid pallet, or individual fluid pallets. As a result, if a portion of the skirt 130 should become depressed, kinked, collapsed, or otherwise compromised during use, only a portion of the fluid pallet (or an individual cell) would be affected, without affecting the entire fluid pallet of the patient support system 100. Such a grid-like skirt 130 configuration is shown in FIG. 1 by way of example only, and it should be understood that the skirt 130 can instead include simply one peripheral skirt 130, for example, positioned between the first portion 126 and the second portion 128 (e.g., if only the most peripheral boundary portion of the skirt 130 were employed). Alternatively, many other suitable multi-skirt configurations are possible that effectively divide the fluid pallet into discrete sections that trap fluid beneath such sections. Other skirt configurations are possible and within the spirit and scope of the present disclosure.

In the embodiment illustrated in FIG. 1, the skirt 130 is formed of a foam tape having a low friction surface (e.g., a closed cell polyethylene foam acrylic adhesive tape, available as Microfoam Tape from 3M Company, St. Paul, Minn.).

In some embodiments, the skirt 130 can be conformable to uneven surfaces (e.g., beds, gurneys, etc.). For example, in some embodiments, the skirt 130 can be formed of a conformable or deformable material, such as an elastomeric seal, closed cell foam, or an inflatable bladder. By employing an inflatable skirt 130, the platform 102 can have a low profile for shipping and storage, but can also have a larger depth when the skirt 130 is inflated to capture fluid and to facilitate moving the platform 102 over uneven surfaces. In embodiments in which the skirt 130 is inflatable, the skirt 130 can be inflated at the same time as the platform 102 is pressurized with fluid from the fluid source 104. That is, in some embodiments, the skirt 130 can also be fluidly coupled to the fluid source 104 directly and/or indirectly (e.g., via the plenum 120). However, in some embodiments, the skirt 130 can be fluidly coupled to a dedicated fluid source. In some embodiments, the skirt 130 can be inflated via a connector (such as tubing) connected to the manifold 108. For example, the skirt 130 can be a section of lay-flat tubing that can be inflated via a fluid conduit connected to one end of the manifold 108. In other embodiments, the inflatable skirt 130 can be a section of sheeting (e.g., a film, e.g., ranging from about 5 cm to 10 cm in width) sealed along both edges to the second surface 112 with excess material between said edges that can be capable of being inflated, for example, via perforations or apertures beneath the sheeting.

In some methods of making the platform 102, the skirt 130 can be inflated prior to being coupled to the platform 102 to inhibit the skirt 130 from being removed from the platform 102 as a result of shear forces that may occur when the skirt 130 is inflated during use. After the skirt 130 is coupled to the platform 102, the skirt 130 can then be deflated for shipping and storage.

In some embodiments, a portion of the platform 102 (e.g., one or both of the first surface 110 and the second surface 112) can include a depression or recess in which the skirt 130 can be positioned when it is coupled to the platform 102.

In some embodiments, the patient support system 100 (or the platform 102) can include additional accessories that can be specific to a desired application. For example, as shown in FIG. 1, in some embodiments, one or more handles 134 can be formed in or coupled to the platform 102 to assist in moving the platform 102 over a fluid pallet, for example, in patient transfer applications. By way of example only, the patient support system 100 includes four, rectangular-shaped apertures or cut-away portions as the handles 134 that are each dimensioned to receive a human hand. However, it should be noted that different types of handles (e.g., rigid handles, flexible handles, etc.) can be employed, and such handles can be coupled to the platform 102, such as to one or both of the first surface 110 and the second surface 112. For example, in some embodiments, the handles 134 can include straps, loops, or the like, that can be coupled to the first surface 110 and/or the second surface 112.

The handles 134 in FIG. 1 are substantially parallel to an edge of the platform 102, as well as to a longitudinal axis of a patient positioned atop the platform 102 during use. However, it should be noted that in some embodiments, the handles 134 can be oriented at an angle with respect to an edge of the platform 102 and/or to a longitudinal axis of the platform (or a longitudinal axis of a patient positioned atop the platform 102) of at least about 20 degrees, in some embodiments, at least about 30 degrees, and in some embodiments about 45 degrees. In some embodiments, the handles 134 can be oriented at an angle of no greater than about 75 degrees, and in some embodiments, no greater than about 60 degrees. In some embodiments, the handles 134 positioned closer to the manifold 108 are oriented symmetrically with respect to the handles 134 positioned further away from the manifold 108, for example, over a symmetry line that bisects the platform 102 parallel to the manifold 108.

In addition, in some embodiments, as shown in FIG. 1, the patient support system 100 can further include straps 136 that can be used to secure a patient to the platform 102 and/or to secure the platform 102 to an underlying surface or structure, such as a bed, table, gurney, or the like.

In some embodiments, the patient support system 100 can further include a system configured to inhibit a phenomenon referred to as "hosing" from occurring; that is, to prevent the clinician from placing a hose emitting warm air directly adjacent a patient's skin. Such a system, for example, can include a valve on the connector 106 and/or a sensor positioned to detect insufficient pressure drop. One example of such a system is described in U.S. Pat. No. 7,338,515, which is incorporated herein by reference.

In some embodiments in which the patient support system 100 is designed for patient transfer applications, the patient support system 100, or a portion thereof, can be designed to remain on a given support surface. For example, in some embodiments, the patient support system 100, or a portion thereof, can be present on most or all support surfaces in a healthcare facility, such as on beds, gurneys, operating room tables, radiological tables, and the like. In such embodiments, a patient can lie on an additional transfer sheet or surface (e.g., the liner 250 of FIG. 2, described below) that is placed on top of the patient support system 100. However, in these embodiments, the patient support system 100 can be placed on the support surface in an inverted position such that fluid exiting the plenum 120 is directed upward away from the support surface and toward the transfer sheet (and patient). Thus, when fluid flow is initiated, the transfer sheet and patient can be elevated on a fluid pallet to facilitate transfer. In this embodiment the transfer sheet may be a passive sheet without a plenum, or the transfer sheet could be an additional patient support system 100 (or portion thereof, such as the platform 102), such that fluid is directed in an opposing manner from both surfaces to further reduce frictional forces involved in the transfer. Whether active or passive, the transfer sheet may be flexible (e.g. a plastic film or fabric), semi-rigid (e.g. a thicker plastic film such as a 100-500 micrometer thick polyolefin), or a rigid sheet (e.g. a thick plastic film (e.g., a polyolefin) having a thickness of greater than 500 micrometers, a transfer board, or the like). The transfer sheet may be flat or contoured, such as a molded plastic sheet. The transfer sheet may have any of the additional features described for the patient support system 100 as well as those described later for other support systems, such as support systems 200 and 300, including but not limited to, a skirt, handles, patient padding, straps and the like.

As a result, in embodiments in which the patient support system 100 is designed to remain coupled to a support surface, the apertures 122 can be positioned to direct flow toward a patient, such that the patient support system 100 can be used for patient transfer and/or patient thermal control.

Figure 2:
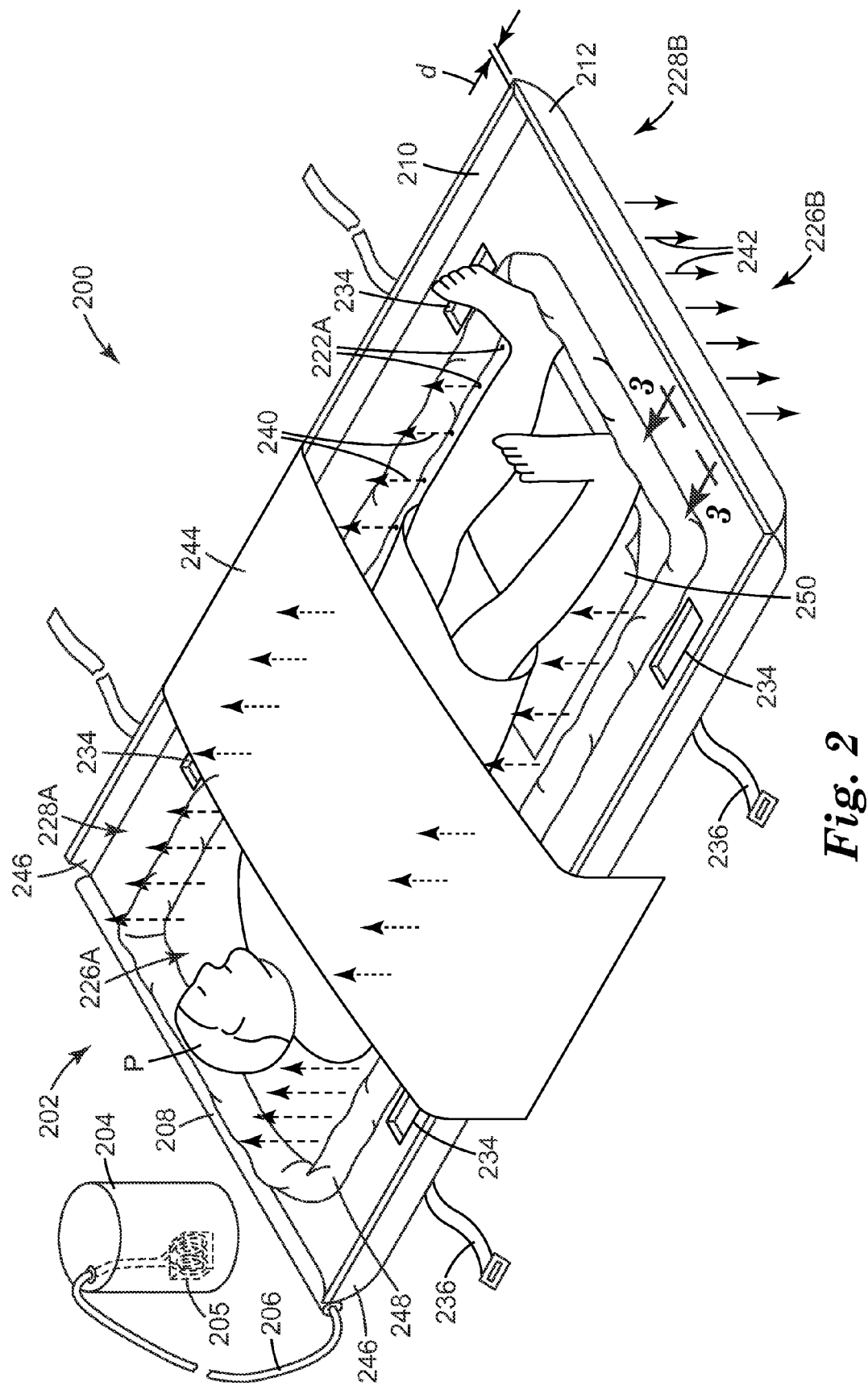
FIG. 2 is a top perspective view of a patient support system according to another embodiment of the present disclosure.

FIGS. 2 and 3 illustrate a patient support system 200 according to another embodiment of the present disclosure, wherein like numerals represent like elements. The patient support system 200 shares many of the same elements and features described above with reference to the illustrated embodiment of FIG. 1. Accordingly, elements and features corresponding to elements and features in the illustrated embodiment of FIG. 1 are provided with the same reference numerals in the 200 series. Reference is made to the description above accompanying FIG. 1 for a more complete description of the features and elements (and alternatives to such features and elements) of the embodiment illustrated in FIGS. 2 and 3.

FIGS. 2 and 3 particularly illustrate a variety of additional accessories or features that may be employed in a patient support system of the present disclosure.

The patient support system 200 is configured for patient transfer and/or patient thermal control. As such, the patient support system 200 includes a platform 202 mechanically coupled and fluidly coupled to a fluid source 204 optionally via a connector 206 (e.g., a hose) and/or a manifold 208. FIG. 3 illustrates the platform 202 in greater detail.

Similar to the embodiment of FIG. 1, the platform 202 of FIGS. 2 and 3 includes a first (top) surface 210 and a second (bottom) surface 212 positioned substantially parallel to the first surface 210 and separated from the first surface 210 by a distance d to provide a chamber or plenum 220 therebetween that is in fluid communication with the fluid source 204. As a result, the plenum 220 can receive fluid under a positive pressure from the fluid source 204. Each of the first surface 210 and the second surface 212 include a major surface that extends in the direction of its length and width and which, in some portions, faces the major surface of the other surface. A patient P is shown positioned atop the platform 102, adjacent the first surface 210.

In addition, the patient support system 200 further includes handles 234 and straps 236 similar to those shown in FIG. 1 and described above.

As shown in FIG. 3, the patient support system 200 can further include supporting structures 214 that can extend at least partially across the distance d or gap between the first surface 210 and the second surface 212. In addition, the supporting structures 214 are shown as being coupled to and integrally formed with both the first surface 210 and the second surface 212, even though this need not be the case. For example, in some embodiments, it is also possible to form a construction in which the supporting structures 214 are not integrally formed or coupled to either the first surface 210 and/or the second surface 212.

As described above, such a platform 202 can be made according to facile manufacturing methods, such as extrusion and/or molding.

The plenum 220 can be at least partially defined by the first surface 210, the second surface 212, and the supporting structures 214. The supporting structures 214 can include an x- and/or y-dimension similar to the supporting structures 114 of FIG. 1 and extend along the length of the platform 202 (e.g., "columnar"), essentially dividing the plenum 220 into a plurality of plenums 220 that are each in fluid communication with the fluid source 204; the supporting structures 214 can be "post-like" or have a length that does not extend along the entire length of the platform 202 such that they define one larger plenum 220; or a combination thereof.

As further shown in FIG. 3, because the patient support system 200 can be configured for use in patient transfer and/or patient thermal control applications, the first surface 210 includes first apertures 222A formed therethrough that can be used for patient warming/cooling, and the second surface 212 includes second apertures 222B formed therein that can be used for patient transfer. As described above, the apertures 222 can be open or valved. By way of example only, the supporting structures 214 and the apertures 222 are shown as being arranged in a regular and repeating array; however, as described above, this need not be the case.

To allow the patient support system 200 to be used for patient thermal control and/or patient transfer, in some embodiments, the fluid source 204 can include or be coupled to a heat transfer (or thermal control) unit 205. The heat transfer unit 205 is shown schematically in FIG. 2 by way of example only, but it should be understood that any suitable heat transfer unit can be employed to either transfer heat into or out of fluid in the plenum 220.

FIG. 2 illustrates arrows 240 in dashed lines representing fluid exiting the first apertures 222A and surrounding the patient P, and arrows 242 in solid lines representing fluid exiting the second apertures 222.

For patient warming and/or cooling applications, the patient support system 200 can include or be used in combination with one or more blankets, drapes, sheets, or the like, such as a blanket 244 shown in FIG. 2 to assist in capturing the temperature controlled fluid exiting the first apertures 222A and surrounding the patient P with the heated fluid. Such a heated fluid can exit the first apertures 222A to convectively heat at least a selected portion of the patient P. For example, as shown in FIG. 2, in some embodiments, the blanket 244 may only cover a portion of the patient P, such that other portions of the patient may remain accessible. In some embodiments, however, for a given procedure, the entire patient P may need to be accessible, in which case, the patient support system 200 may not include or be used in combination with any blankets or drapes.

In some embodiments, the apertures 222 can include a variety of apertures 222 of varying shapes and sizes. For example, in some embodiments, the first apertures 222A can include one or more large exhaust ports to increase the flow rate of the temperature-controlled fluid that is used to warm or cool the patient P. Similarly, in some embodiments, such larger apertures can be employed in the second apertures 222B to assist in attaining the desired lift of the patient P.

As described above with respect to the embodiment illustrated in FIG. 1, the first apertures 222A and the second apertures 222B need not be formed over the entire respective surfaces of the first surface 210 and the second surface 212. Rather, as shown in FIG. 2, in some embodiments, the first apertures 222A can be formed in a first portion 226A of the first surface 210 and not in a second portion 228A of the first surface 210, and the first apertures 222B can be formed in a first portion 226B of the second surface 212 and not in a second portion 228B of the second surface 212. The first portion 226A of the first surface 210 need not correspond with the first portion 226B of the second surface 212, but it may correspond in some embodiments, and the second portion 228A of the first surface 210 need not correspond with the second portion 228B of the second surface 212, but it may correspond in some embodiments.

In some embodiments, the patient support system 200 includes all of the features necessary to be used either for patient transfer or patient thermal control. In such embodiments, for example, the second apertures 222B can include or be coupled to pressure-activated valves, such that fluid will not exit the second apertures 222B until a cracking pressure in the plenum 220 has been reached. The plenum 220 can be controlled by a control unit that would deliver, on demand, either (i) low pressure heated fluid (e.g., at a temperature of about 35-42° C.) or low pressure chilled fluid (e.g., in some embodiments, having a temperature ranging from 2-20° C., and in some embodiments, ranging from 4-15° C.) that would flow into the plenum 220 and out the first apertures 222A for patient warming or cooling, or (ii) high pressure cool fluid (e.g., at ambient temperature) that would flow into the plenum 220 and out the second apertures 222B for patient transfer. In such embodiments, the low pressure heated or chilled fluid can be adapted to have either insufficient pressure to activate the valves of the second apertures 222B or, if valves are not employed, insufficient pressure to lift the platform 202 when the patient P is positioned on top of the platform 202. The non-temperature-controlled fluid (e.g., at ambient temperature), however, would have a sufficient pressure either to activate the valves of the second apertures 222B or to lift the platform 202 and the patient P.

In other embodiments, the patient support system 200 can be configured to provide patient transfer and patient thermal control simultaneously. In some embodiments, this can be accomplished merely by employing two platforms 202—one with the first apertures 222A and another with the second apertures 222B. In such embodiments, the second surface 212 of one platform 202 can be optionally coupled to the first surface 210 of the other platform 202.

Figure 5:
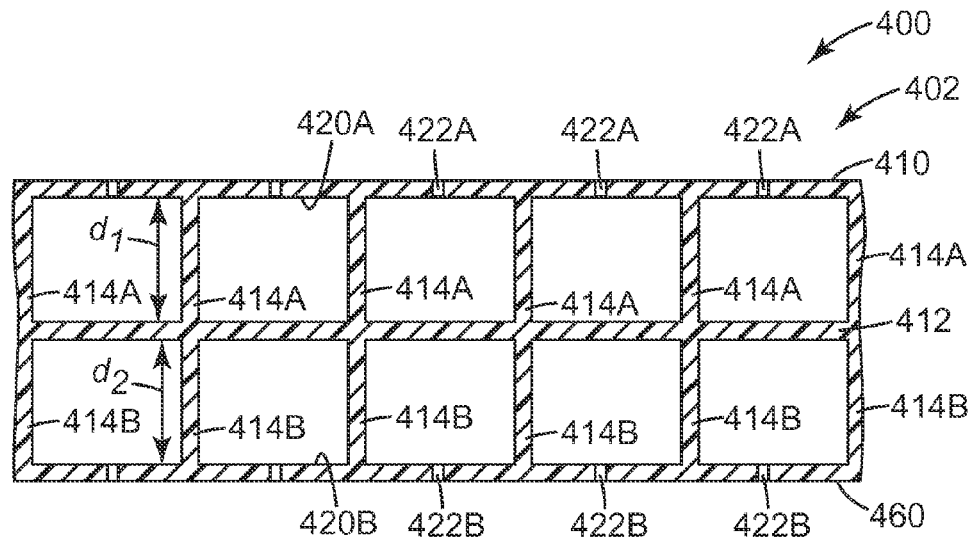
FIG. 5 is cross-sectional view of a patient support system according to another embodiment of the present disclosure, comprising a dual plenum.
Figure 9:
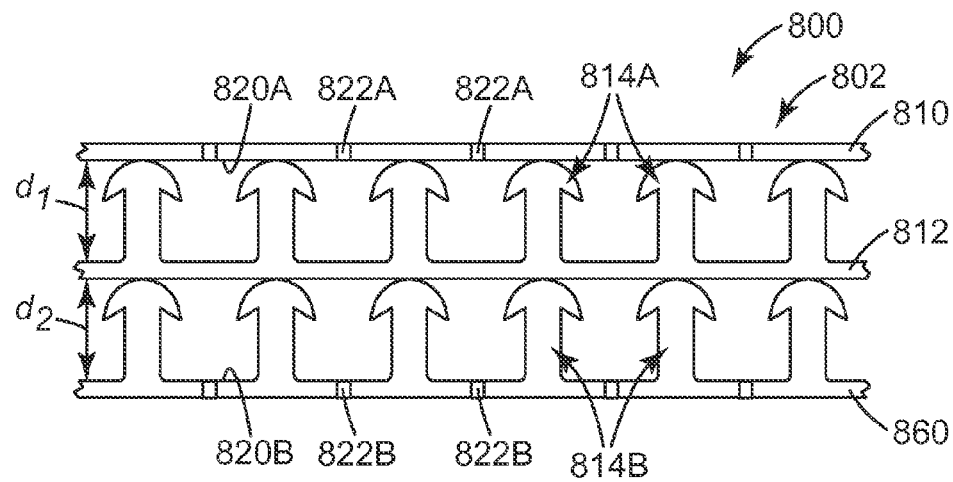
FIG. 9 is a schematic cross-sectional view of a patient support system according to another embodiment of the present disclosure, comprising a dual plenum.
Figure 10:
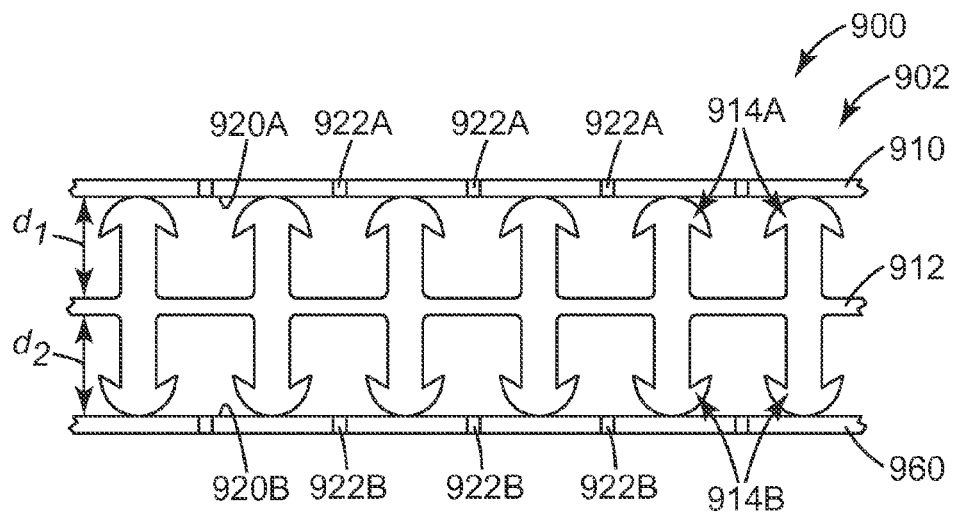
FIG. 10 is a schematic cross-sectional view of a patient support system according to another embodiment of the present disclosure, comprising a dual plenum.

In still other embodiments, in order to be able to provide patient transfer and patient thermal control simultaneously, a system comprising a dual plenum configuration can be employed, where one or more first plenum(s) are configured to provide patient warming/cooling, and one or more second plenum(s) are configured to provide patient transfer. Examples of such systems are shown in FIGS. 5, 9 and 10 and described below.

As shown in FIG. 2, in some embodiments, the platform 202 can include curved edges 246 to avoid snagging the edges of the platform 202 on surfaces or objects (e.g., bed linens), for example, during patient transfer. As shown in FIG. 2, in some embodiments, the curved edges 246 can be curved upwardly, toward the first surface 210. In some embodiments, the platform 202 can include edges that are curved downwardly toward the second surface 212, and such edges can be used in addition to or in lieu of a skirt (such as the skirt 130 of FIG. 1 described above) to assist in directing fluid flow and lifting the platform 202 and the patient P away from a surface in patient transfer.

As further shown in FIG. 2, in some embodiments, the patient support system 200 (or the platform 202) can further include a rim structure 248 positioned toward a periphery of the first surface 210 to inhibit the patient P from falling off of the platform 202. The rim structure 248 can be formed of a variety of materials. In some embodiments, the rim structure 248 can be a rigid wall or ledge, and in some embodiments, as shown in FIG. 2, the rim structure 248 can include be conformable or deformable. For example, in some embodiments, the rim structure 248 can be formed of a deformable material, such as a closed cell foam or an inflatable bladder. By employing an inflatable rim structure 248, the platform 102 can have a low profile for shipping and storage, but can include the rim structure 248 as a safety feature during use. In embodiments in which the rim structure 248 is inflatable, the rim structure 248 can be inflated at the same time as the platform 102 is pressurized with fluid from the fluid source 204. That is, in some embodiments, the rim structure 248 can also be fluidly coupled to the fluid source 204 directly and/or indirectly (e.g., via the plenum 220). However, in some embodiments, the rim structure 248 can be fluidly coupled to a dedicated fluid source. In some embodiments, the rim structure 248 can be formed from one or more segments of lay-flat tubing which has been attached to the platform 202 (e.g., similar to the skirt 130 described above). In other embodiments, the rim structure 248 can be a section of sheeting (e.g., a film, e.g., ranging from about 5 cm to 10 cm in width) sealed along both edges to the first surface 110 with excess material between said edges that can be capable of being inflated, for example, via perforations or apertures beneath the sheeting.

Similarly, the patient support system 200 can include additional padding or inflatable bladders that can be coupled to the first surface 210 wherever necessary to afford additional padding under desired portions of the patient P, such as the head, the hips, the heels, or the like.

As further shown in FIG. 2, in some embodiments, the patient support system 200 (or the platform 202) can further include one or more liners or covers 250. Such liners 250 can be disposable, can be of a variety of shapes and sizes, and can be adapted for several different uses. For example, as shown in FIG. 2, in some embodiments, the liner 250 need not extend over a majority of the first surface 210, but rather can be positioned just under a portion of the patient P. In some embodiments, the liner 250 can include a low friction surface and can be used as a slip sheet to facilitate loading a patient (e.g., an immobile or non-ambulatory patient) onto the first surface 210 of the platform 202. In other embodiments, the liner 250 can be absorbent and capable of absorbing platform fluids.

In some embodiments, the liner 250 can include a fluid blocking layer that can be positioned adjacent at least some of the apertures 222 to selectively block fluid flow out of some of the apertures 222. This can be used, for example, to block certain areas of the patient P from the convective warming. In some embodiments, the patient support system 200 can include the liner 250 covering all of the first apertures 222A, and the liner 250 can include perforations at various positions along its length, such that a clinician can decide where to remove the liner 250 to expose the desired portions of the patient P to the heated or cooled/chilled fluid.

In some embodiments, multiple liners 250 can be employed, and the multiple liners 250 can include slip sheets, absorbents, fluid blocking layers, or a combination thereof.

As shown in FIG. 3, in some embodiments, the patient support system 200 can further include a plurality of support projections 254 (not shown in FIG. 2), which can be posts, rails, or the like, similar to the supporting structures 214. The support projections 254 can be formed by microreplication and can be coupled to the first surface 210 to essentially present a "bed of nails" surface to the patient P. Such a support surface for the patient P can provide exceptional fluid circulation (both from the first apertures 222A and of the air surrounding the patient P) beneath and/or around the patient P. The plurality of support projections 254 can also provide a substantially low friction surface to the patient, without comprising "breathability" or fluid circulation. Similar to the supporting structures 214, the support projections 254 can be formed of any shape or size necessary and can be arranged in any suitable configuration. Unlike the supporting structures 214 within the platform 202, however, the support projections 254 are adapted to face the patient P and are positioned to be exposed to ambience.

Figure 4:
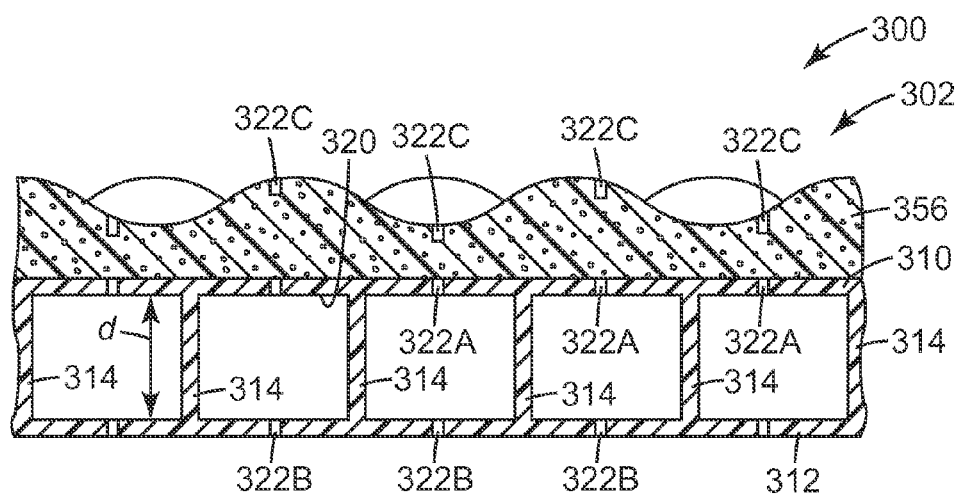
FIG. 4 is a cross-sectional view of a patient support system according to another embodiment of the present disclosure.

FIG. 4 illustrates at least a portion of a patient support system 300 according to another embodiment of the present disclosure, wherein like numerals represent like elements. The patient support system 300 shares many of the same elements and features described above with reference to the illustrated embodiments of FIGS. 1-3. Accordingly, elements and features corresponding to elements and features in the illustrated embodiments of FIGS. 1-3 are provided with the same reference numerals in the 300 series. Reference is made to the description above accompanying FIGS. 1-3 for a more complete description of the features and elements (and alternatives to such features and elements) of the embodiment illustrated in FIG. 4.

The patient support system 300 can be configured for patient transfer and/or patient thermal control, and includes a platform 302 that is substantially the same as the platform 202 of the patient support system 200 shown in FIGS. 2 and 3 and described above. As such, the platform 302 includes a first (top) surface 310 and a second (bottom) surface 312 positioned substantially parallel to the first surface 310 and separated from the first surface 310 by a distance d to provide a chamber or plenum 320 therebetween. The platform 302 can further include supporting structures 314 that can extend at least partially across the distance d or gap between the first surface 310 and the second surface 312. In addition, the supporting structures 314 are shown as being coupled to and integrally formed with both the first surface 310 and the second surface 312.

Similar to the platform 202 shown in FIG. 3, the first surface 310 of the platform 302 can include first apertures 322A formed therethrough that can be used for patient thermal control, and the second surface 312 can include second apertures 322B formed therein that can be used for patient transfer.

As shown in FIG. 4, the patient support system 300 can further include a conformable body 356 that can be coupled to the first surface 310 to provide a conformable and potentially more comfortable and pressure-distributing support surface for a patient. The conformable body 356 can be formed of a conformable or deformable material, such as foams, gels, or one or more inflatable bladders, as well as a combination thereof. As a result, the conformable body 356 can serve to prevent a patient from developing pressure ulcers. In some embodiments, the conformable body 356 can be treated with one or more antimicrobial agents to kill microbes, for example, to improve hygiene and reduce odor.

The conformable body 356 can be formed of a variety of materials, including, but not limited to, one or more of open cell foams, fabrics (e.g., nonwoven, woven, knit, or combinations thereof), gel pads, or combinations thereof.

By employing an inflatable conformable body 356, the platform 302 can have a low profile for shipping and storage, but can also have a larger depth when the conformable body 356 is inflated during use. In embodiments in which the conformable body 356 is inflatable, the conformable body 356 can be inflated at the same time as the platform 302 is pressurized with fluid. That is, in some embodiments, the conformable body 356 can also be fluidly coupled to the same fluid source to which the platform 302 is coupled, either directly and/or indirectly (e.g., via the plenum 320). However, in some embodiments, the conformable body 356 can be fluidly coupled to a dedicated fluid source.

In embodiments adapted for patient transfer, because a fluid pallet formed under the platform 302 would not be dependent on the level of inflation of the conformable body 356, a fluid pallet can still be created under the platform 302 relatively quickly, without requiring that the conformable body 356 fully inflate to a sufficient internal pressure. Rather, the conformable body 356 can be inflated independently of the need for a fluid pallet, as needed. Even in embodiments in which the conformable body 356 is inflated by the same fluid source as the platform 302 is pressurized, one or more valves can be used to close off fluid paths into the conformable body 356, if necessary, in order to deliver the fluid solely to the platform 302. In addition, after inflation, the valve(s) controlling flow into the conformable body 356 can be closed to prevent deflation of the conformable body 356.

In some embodiments, as shown in FIG. 4, the conformable body 356 can include third apertures 322C that can either be provided by the material makeup of the platform 356 (e.g., a porous material) or can be formed in the platform 356. Such third apertures 322C can fluidly communicate with the first apertures 322A, such that patient thermal control (i.e., warming and/or cooling) can still be provided even in embodiments employing the conformable body 356.

Furthermore, in some embodiments, the conformable body 356 can be configured to provide pulsation therapy to a patient to move the patient while positioned on the platform 302, and to inhibit the development of pressure ulcers.

In some embodiments, the conformable body 356 of FIG. 4. can be combined with the support projections 254 of FIG. 3 so that the conformable body 356 would always remain above the first surface 210 or 310 by at least the height of the support projections 254. That is, the support projections 254 would prevent an upper surface or portion of the conformable body 356 from completely compressing to the point of contacting the first surface 210 or 310.

FIG. 5 illustrates at least a portion of a patient support system 400 according to another embodiment of the present disclosure, wherein like numerals represent like elements. The patient support system 400 shares many of the same elements and features described above with reference to the illustrated embodiments of FIGS. 1-3. Accordingly, elements and features corresponding to elements and features in the illustrated embodiments of FIGS. 1-3 are provided with the same reference numerals in the 400 series. Reference is made to the description above accompanying FIGS. 1-3 for a more complete description of the features and elements (and alternatives to such features and elements) of the embodiment illustrated in FIG. 5.

The patient support system 400 is configured for patient transfer and/or patient thermal control (e.g., warming or cooling), and includes a platform 402 that is substantially the same as the platform 202 of the patient support system 200 shown in FIGS. 2 and 3 and described above, except that the platform 402 includes a dual-plenum configuration, as mentioned above. As such, the platform 402 includes a first surface 410, a second surface 412 that forms an innermost layer, and a third surface 460. The second surface 412 can be positioned substantially parallel to the first surface 410 and separated from the first surface 410 by a first distance $d_1$ to provide one or more first plenums 420A therebetween. The third surface 460 can be positioned substantially parallel to the first surface 410 and the second surface 412 and positioned on the opposite side of the second surface 412 from the first surface 410. The third surface 460 can be separated from the second surface 412 by a second distance $d_2$ to provide one or more second plenums 420B. The platform 402 can further include a plurality of first supporting structures 414A that can extend at least partially across the first distance $d_1$ or gap between the first surface 410 and the second surface 412 and a plurality of second supporting structures 414B that can extend at least partially across the second distance $d_2$ or gap between the second surface 412 and the third surface 460. In addition, all of the supporting structures 414 are shown as being coupled to and integrally formed with both the first surface 410, the second surface 412, and the third surface 460, even though this need not be the case. As mentioned above, in some embodiments, it is also possible to form a construction similar to the platform 402 by stacking and optionally bonding together two identical or uniquely constructed platforms (such as the platforms 102 of FIG. 1).

Furthermore, as shown in FIG. 5, the first surface 410 of the platform 402 can include first apertures 422A formed therethrough that can be used for patient warming and/or cooling, and the third surface 460 can include second apertures 422B formed therein that can be used for patient transfer.

In such embodiments, the patient transfer and patient thermal control operations can be completely independent from one another, such that patient transfer and patient thermal control can be provided separately or simultaneously, depending on the need for a given patient or procedure.

In some embodiments, the platform 402 having the dual plenum configuration can be formed by extrusion and/or molding. In some embodiments, only a portion of the platform 402 is integrally formed, such as the first surface 410, the second surface 412, the first supporting structures 414A and the second supporting structures 414B, and the third surface 460 can then be coupled to the second supporting structures 414B by a variety of methods, such as by using a gap-controlled heated nip roller.

In some embodiments, the patient support system 400 need not include the first apertures 422A for convective patient thermal control. Rather, a patient thermal control system can be employed in which a temperature-controlled (e.g., heated or chilled) fluid (e.g., a liquid) is provided in the first plenum(s) 420A beneath a patient, to radiantly heat or cool the patient. In such embodiments, the first plenum(s) 420A can be in fluid communication with a heat transfer (or thermal control) unit that is configured to thermally control the fluid (i.e., transfer heat into or out of the fluid) in the first plenum(s) 420A. In addition, in some embodiments, the fluid can be recycled or recirculated from the first plenum(s) 420A back to the heat transfer unit. Such a heat transfer unit can be coupled to or form a portion of a dedicated fluid source that can operate independently of another fluid source in fluid communication with the second plenum(s) 420B. As a result, the second plenum(s) 420B and the second apertures 422B can be employed for another application, such as patient transfer.

The terms "first" surface, "second" surface and "third" surface are used and arranged in the figures by way of example only; however, it should be understood that the top surface 410 can instead be referred to as the second surface or the third surface, the middle surface 412 can instead be referred to as the first surface or the third surface, and so on.

Other dual plenum configurations are shown in FIGS. 9 and 10 and described below.

Figure 6A:
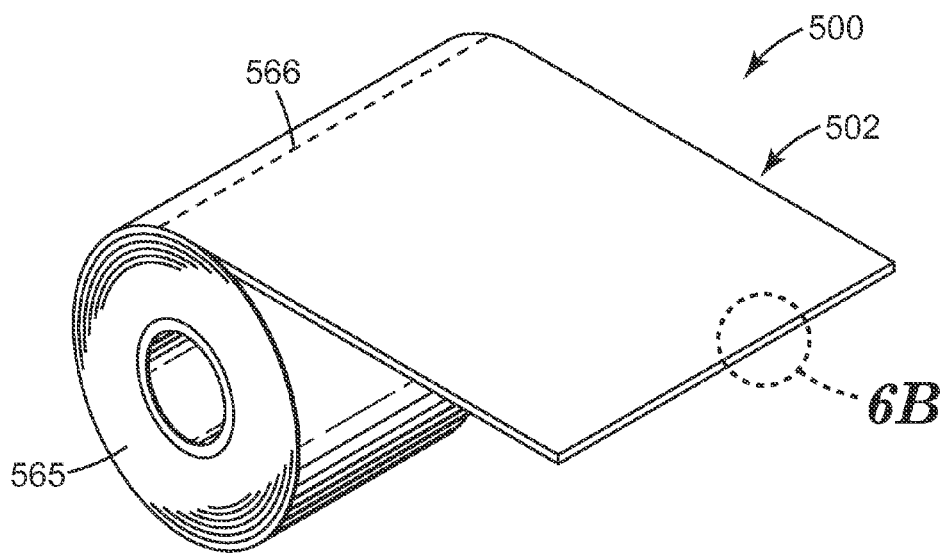
FIG. 6A is a patient support system according to another embodiment of the present disclosure, the patient support system including a platform provided in rolled form.
Figure 6B:
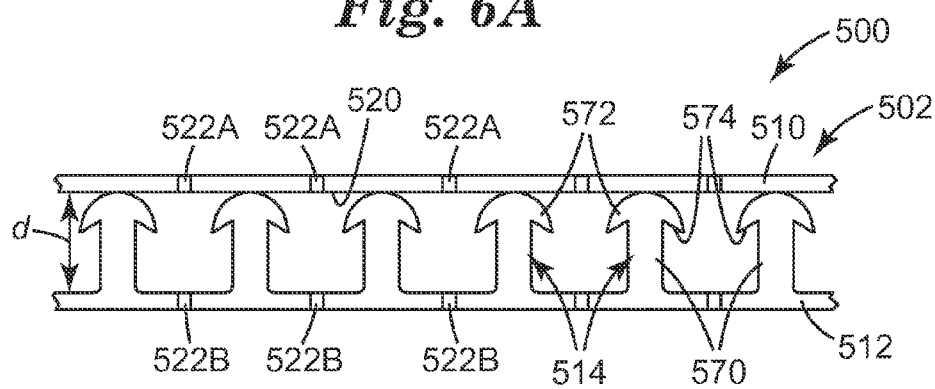
FIG. 6B is a schematic cross-sectional view of the patient support system of FIG. 6A.

FIGS. 6A and 6B illustrate at least a portion of a patient support system 500 according to another embodiment of the present disclosure, wherein like numerals represent like elements. The patient support system 500 shares many of the same elements and features described above with reference to the illustrated embodiments of FIGS. 1-3. Accordingly, elements and features corresponding to elements and features in the illustrated embodiments of FIGS. 1-3 are provided with the same reference numerals in the 500 series. Reference is made to the description above accompanying FIGS. 1-3 for a more complete description of the features and elements (and alternatives to such features and elements) of the embodiment illustrated in FIGS. 6A and 6B.

The patient support system 500 can be configured for patient transfer and/or patient thermal control and includes a flexible platform 502. As such, as shown in FIG. 6A, the platform 502 can be provided in a roll 565, and can include perforations 566 along its length, such that desired amounts of the platform 502 can be removed and used for a particular application (e.g., to suit different patient sizes or different uses).

As shown in FIG. 6B, the platform 502 includes a first (top) surface 510 and a second (bottom) surface 512 positioned substantially parallel to the first surface 510 and separated from the first surface 510 by a distance d to provide a chamber or plenum 520 therebetween. As shown, the platform 502 can further include supporting structures 514 that are integrally formed with the second surface 512 and that can extend at least partially across the distance d or gap between the first surface 510 and the second surface 512. As a result of the supporting structures 514 being integrally formed with the second surface 512, at least the second surface 512 and the supporting structures 514 can be provided by a facile manufacturing method such as extrusion and/or molding. In some embodiments, the supporting structures 514 can also be integrally formed with the first surface 510, but in the embodiments illustrated in FIG. 6B, the first surface 510 is formed separately and can then be coupled to the tops of the supporting structures 514, for example, using a gap-controlled heated nip roller to bond the first surface 510 to the tops of the supporting structures 514.

Similar to some of the embodiments described above, the first surface 510 of the platform 502 can include first apertures 522A formed therethrough that can be used for patient thermal control, and the second surface 512 can include second apertures 522B formed therein that can be used for patient transfer.

The supporting structures 514 are an example of an alternatively-shaped supporting structure. The supporting structures 514 each include a stem 570 and a cap 572, similar to the structure of interlocking hooks that have been used in various fastener systems. The stem 570 and the cap 572 of each supporting structure 514 can be formed of the same or a different material. For example, in some embodiments, the cap 572 can be formed of a material having a lower melting point than the material that forms the stems 570, such that the caps 572 can at least partially function as an adhesive (e.g., a low melting adhesive or a hot-melt adhesive) to bond the supporting structures 514 to the first surface 510. For example, in some embodiments, the caps 572 can be formed of ENGAGE and/or AFFINITY polyolefin (available from Dow Chemical Company, Midland, Mich.), and the stems 570 can be formed of TOTAL polypropylene (available from Total Petrochemicals, Houston, Tex.). In this manner, the caps 572 can have a lower melting point than the stems 570 of the supporting structures 514, which can facilitate thermally bonding the first surface 510 to the caps 572. Such constructions can be formed, for example, by a co-extrusion process.

In addition, the cap 572 of each supporting structure 514 can include one or more flanges 574 that can be adapted to engage one or more structures of the platform 502, as described in greater detail below with reference to FIG. 8.

As shown in FIG. 6B, the caps 572 include a shroud-like or mushroom-like shape (such as those disclosed in U.S. Pat. No. 5,077,870). However, caps 572 having other shapes can also be employed, including, but not limited to, j- or hook-shaped caps 572, flat-head caps 572 (such as those disclosed in U.S. Pat. No. 5,679,302), flat-head caps 572 having grooves formed in their top surface (such as those disclosed in U.S. Pat. No. 6,000,106), spherical caps 572, hemi-spherical caps 572, other suitably shaped caps 572, or a combination thereof. Each reference mentioned above is incorporated herein by reference.

The supporting structures 514 can be formed by a variety of methods, such as those described in the references mentioned above, extrusion (e.g., profile extrusion), co-extrusion, molding, splicing, stretching, microreplication, and a combination thereof. An example of a profile extrusion process is described in U.S. Pat. No. 6,106,922 (Cejka et al.), U.S. Pat. No. 3,586,220 (Reinsberg), U.S. Pat. No. 4,894,060 (Nestegard), U.S. Pat. No. 4,187,068 (Vassar), and U.S. Pat. No. 3,422,648 (Lemelson), which are incorporated herein by reference.

In some embodiments, an exemplary profile extrusion process can include one or more single or twin screw extruders that melt and convey polymeric resin in a molten state to an extrusion die. The extrusion die can express the molten polymer in a defined geometrical shape or profile. For example, a cross sectional profile resembling a square sine wave can be coupled to a base rectangle, which would produce an elongate polymeric article having an elongated base in which columns, ridges and/or channels are formed. The molten shaped polymer is then quickly cooled before it can relax its shape. Cooling can be done by extruding the polymer directly into a heat transfer fluid such as temperature-controlled water.

In some embodiments, the supporting structures 514 can extend along an x- or a y-direction (i.e., along a major surface of one or both of the first surface 510 and the second surface 512), in addition to extending along a z-direction between the first surface 510 and the second surface 512, forming a rail- or columnar-like shape. In embodiments in which the supporting structures 514 are columnar, the plenum 520 can be divided into a plurality of plenums 520, as described above with respect to the supporting structures 114 of FIG. 1.

In some embodiments, the first surface 510 can include a non-porous, microporous, or perforated/apertured material that can be bonded to the caps 572 of the supporting structures 514.

Figure 7:
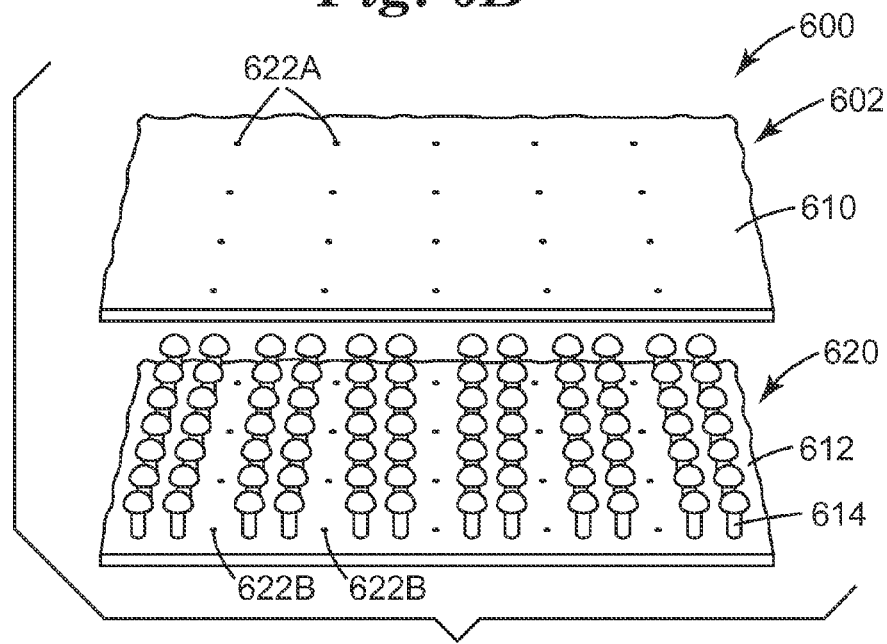
FIG. 7 is an exploded view of a patient support system according to another embodiment of the present disclosure.

FIG. 7 illustrates at least a portion of a patient support system 600 according to another embodiment of the present disclosure, wherein like numerals represent like elements. The patient support system 600 shares many of the same elements and features described above with reference to the illustrated embodiments of FIGS. 1-3 and FIGS. 6A-6B. Accordingly, elements and features corresponding to elements and features in the illustrated embodiments of FIGS. 1-3 and FIGS. 6A-6B are provided with the same reference numerals in the 600 series. Reference is made to the description above accompanying FIGS. 1-3 and 6A-6B for a more complete description of the features and elements (and alternatives to such features and elements) of the embodiment illustrated in FIG. 7.

The patient support system 600 can be configured for patient transfer and/or patient thermal control, and includes a platform 602 that is substantially the same as the platform 502 of the patient support system 500 shown in FIGS. 6A and 6B and described above. As such, the platform 602 includes a first (top) surface 610 and a second (bottom) surface 612 adapted to be positioned substantially parallel to the first surface 610 and separated from the first surface 310 by a gap to provide a chamber or plenum 620 therebetween. The platform 602 can further include supporting structures 614 that can extend at least partially across the gap between the first surface 610 and the second surface 612. The supporting structures 614 are substantially the same as the supporting structures 514 of FIGS. 6A-6B and are also in the form of interlocking hooks. The supporting structures 614 are also shown as being integrally formed with the second surface 612. FIG. 7 shows an exploded view before the first surface 610 has been coupled to the supporting structures 614.

Similar to the platform 502 shown in FIGS. 6A-6B, the first surface 610 of the platform 602 can include first apertures 622A formed therethrough that can be used for patient convective thermal control, and the second surface 612 can include second apertures 622B formed therein that can be used for patient transfer (e.g., creating a low friction fluid pallet). The apertures 622 can be formed before or after the first surface 610 is bonded to the second surface 612.

The supporting structures 614 are shown by way of example only as having a post-like rather than a channel- or column-like shape. In addition, by way of example only, the supporting structures 614 are shown as begin arranged in rows having a width formed by two supporting structures 614, similar to the configuration of 3M DUAL LOCK interlocking hooks (available from 3M Company, St. Paul, Minn.).

The shapes and configurations of the interlocking hook-type supporting structures 514 and 614 of FIGS. 6A-6B and 7, respectively, are shown by way of example only; however, it should be understood that a variety of shapes, arrangements and configurations of interlocking hook-type supporting structures 514 and 614 can be employed without departing from the spirit and scope of the present disclosure.

Figure 8:
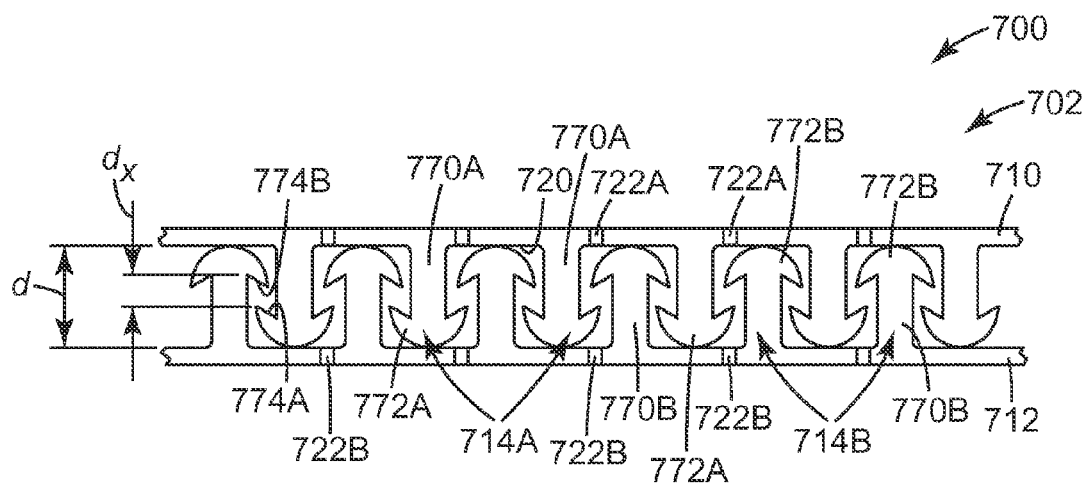
FIG. 8 is a schematic cross-sectional view of a patient support system according to another embodiment of the present disclosure.

FIG. 8 illustrates at least a portion of a patient support system 700 according to another embodiment of the present disclosure, wherein like numerals represent like elements. The patient support system 700 shares many of the same elements and features described above with reference to the illustrated embodiments of FIGS. 1-3 and FIGS. 6A-7. Accordingly, elements and features corresponding to elements and features in the illustrated embodiments of FIGS. 1-3 and FIGS. 6A-7 are provided with the same reference numerals in the 700 series. Reference is made to the description above accompanying FIGS. 1-3 and 6A-7 for a more complete description of the features and elements (and alternatives to such features and elements) of the embodiment illustrated in FIG. 8.

The patient support system 700 can be configured for patient transfer and/or patient thermal control, and includes a platform 702 that includes a first (top) surface 710 and a second (bottom) surface 712 adapted to be positioned substantially parallel to the first surface 710 and separated from the first surface 710 by at least a distance of d to provide a chamber or plenum 720 therebetween. The platform 702 can further include first supporting structures 714A that are coupled to (and by way of example only, integrally formed with) the first surface 710 and that can extend at least partially across the distance d between the first surface 710 and the second surface 712. As shown, the platform 702 can further include second supporting structures 714B that are coupled to (and by way of example only, integrally formed with) the second surface 712 and that can also extend at least partially across the distance d between the first surface 710 and the second surface 712. The first supporting structures 714A and the second supporting structures 714B are shown as including an interlocking hook shape, and can include any of the features (and alternatives thereto) described above with respect to the supporting structures 514 and 614 of FIGS. 6A-6B and 7, respectively.

Each of the first supporting structures 714A includes a first stem 770A and a first cap 772A. Similarly, each of the second supporting structures 714B includes a second stem 770B and a second cap 772B. As shown, the first caps 772A can be configured to engage (e.g., interlock with) the second caps 772B as a means for coupling the first surface 710 and the second surface 712 while providing a gap therebetween for one or more plenum(s) 720. As a result, each first cap 772A can come into contact with the second surface 712, and each second cap 772B can come into contact with the first surface 710. In addition, the platform 702 can be formed by coupling the first supporting structures 714A and the second supporting structures 714B.

More specifically, each first cap 772A can include one or more first flanges 774A that can engage with one or more second flanges 774B of one or more of the second caps 772B. As a result, when the first surface 710 and the second surface 712 are pressed toward one another such that the first caps 772A contact the second surface 712 and the second caps 772B contact the first surface 710, the first surface 710 and the second surface 712 can be positioned the distance d apart. When the first surface 710 and the second surface 712 are positioned the distance d apart, the first flange(s) 774A can be positioned a distance $d_x$ from the second flange(s) 774B, as shown in FIG. 8.

However, in the embodiment illustrated in FIG. 8, the first surface 710 and the second surface 712 need not be positioned a fixed distance apart, and the first surface 710 can separate from the second caps 772B and the second surface 712 can separate from the first caps 772A, such that the first surface 710 and the second surface 712 can be positioned a total distance $d+d_x$ apart from one another. In use, when a patient is positioned atop the first surface 710, the material makeup and structure of the platform 702 will support the patient's weight and the first surface 710 and the second surface 712 will be positioned about a distance d apart. When the patient is removed, the first surface 710 and the second surface 712 can separate slightly, such that at least in some portions, the first surface 710 can be separated from the second surface 712 by a distance of up to about the total distance $d+d_x$.

Such a construction can avoid the need to bond one of the first and second surfaces 710 or 712 to the caps 772 of the opposite surface 712 or 710.

The first surface 710 of the platform 702 can further include first apertures 722A formed therethrough that can be used for patient thermal control, and the second surface 712 can include second apertures 722B formed therein that can be used for patient transfer. The apertures 722 can be formed before or after the first supporting structures 714A are coupled to (e.g., interengaged with) the second supporting structures 714B.

FIG. 9 illustrates at least a portion of a patient support system 800 according to another embodiment of the present disclosure, wherein like numerals represent like elements. The patient support system 800 shares many of the same elements and features described above with reference to the illustrated embodiments of FIGS. 1-3, 5, 6A-6B and 7. Accordingly, elements and features corresponding to elements and features in the illustrated embodiments of FIGS. 1-3, 5, 6A-6B and 7 are provided with the same reference numerals in the 800 series. Reference is made to the description above accompanying FIGS. 1-3, 5, 6A-6B and 7 for a more complete description of the features and elements (and alternatives to such features and elements) of the embodiment illustrated in FIG. 9.

The patient support system 800 can be configured for patient transfer and/or patient thermal control. The patient support system 800 can include a platform 802 that is substantially similar to the platform 502 of FIGS. 6A-6B, except that the platform 802 includes a dual plenum configuration, similar to the platform 402 of FIG. 5.

As such, the platform 802 includes a first surface 810, a second surface 812 that forms an innermost layer, and a third surface 860. The second surface 812 can be positioned substantially parallel to the first surface 810 and separated from the first surface 810 by a first distance $d_1$ to provide one or more first plenums 820A. The third surface 860 can be positioned substantially parallel to the first surface 810 and the second surface 812 and positioned on the opposite side of the second surface 812 from the first surface 810. The third surface 860 can be separated from the second surface 812 by a second distance $d_2$ to provide one or more second plenums 820B.

The platform 802 can further include a plurality of first supporting structures 814A that can extend at least partially across the first distance $d_1$ or gap between the first surface 810 and the second surface 812, and which are shown by way of example only to be integrally formed with the second surface 812, similar to the platform 502 of FIGS. 6A and 6B. The first surface 810 can be coupled to the first supporting structures 814A as described above with respect to FIGS. 6A and 6B.

The platform 802 can further include a plurality of second supporting structures 814B that can extend at least partially across the second distance $d_2$ or gap between the second surface 812 and the third surface 860, and which are shown by way of example only to be integrally formed with the third surface 860. The second surface 812 can be coupled to the second supporting structures 814B in a similar manner that the first surface 810 is coupled to the first supporting structures 814A. The first surface 810 can be coupled to the first supporting structures 814A at the same time that the second surface 812 is coupled to the second supporting structures 814B, or these coupling steps can be performed sequentially.

Furthermore, the first surface 810 of the platform 802 can include first apertures 822A formed therethrough that can be used for patient convective thermal control, and the third surface 860 can include second apertures 822B formed therein that can be used for patient transfer.

In such embodiments, the patient transfer and patient warming/cooling operations can be completely independent from one another, such that patient transfer and patient warming/cooling can be provided separately or simultaneously, depending on the need for a given patient or procedure.

In some embodiments, the structure comprising the second surface 812 and the first supporting structures 814A and the structure comprising the third surface 860 and the second supporting structures 814B can each be formed by extrusion and/or molding. Then, the first surface 810 can be coupled to the first supporting structures 814A, and the second surface 812 can be coupled to the second supporting structures 814B, by a variety of methods, such as by using a gap-controlled heated nip roller.

FIG. 10 illustrates at least a portion of a patient support system 900 according to another embodiment of the present disclosure, wherein like numerals represent like elements. The patient support system 900 shares many of the same elements and features described above with reference to the illustrated embodiments of FIGS. 1-3, 5, 6A-6B, 7 and 8. Accordingly, elements and features corresponding to elements and features in the illustrated embodiments of FIGS. 1-3, 5, 6A-6B, 7 and 8 are provided with the same reference numerals in the 900 series. Reference is made to the description above accompanying FIGS. 1-3, 5, 6A-6B, 7 and 8 for a more complete description of the features and elements (and alternatives to such features and elements) of the embodiment illustrated in FIG. 10.

The patient support system 900 can be configured for patient transfer and/or patient thermal control. The patient support system 900 can include a platform 902 that is substantially similar to the platform 802 of FIG. 9. As such, the platform 902 includes a first surface 910, a second surface 912 that forms an innermost layer, and a third surface 960. The second surface 912 can be positioned substantially parallel to the first surface 910 and separated from the first surface 910 by a first distance $d_1$ to provide one or more first plenums 920A. The third surface 960 can be positioned substantially parallel to the first surface 910 and the second surface 912 and positioned on the opposite side of the second surface 912 from the first surface 910. The third surface 960 can be separated from the second surface 912 by a second distance $d_2$ to provide one or more second plenums 920B.

In the platform 802 of FIG. 9, the first supporting structures 814A extend from the second surface 812 toward the first surface 810 and the second supporting structures 814B extend from the third surface 860 toward the second surface 812. However, the platform 902 of FIG. 10 includes first supporting structures 914A that are coupled to (e.g., integrally formed with) the second surface 912 and which extend from the second surface 912 toward the first surface 910, as well as second supporting structures 914B that are also coupled to (e.g., integrally formed with) the second surface 912 and which extend from the second surface 912 toward the third surface 960.

As a result, in some embodiments, the structure comprising the second surface 912 and the first and second supporting structures 914A and 914B can each be formed by extrusion and/or molding. The first surface 910 can be coupled to the first supporting structures 914A and the third surface 960 can be coupled to the second supporting structures 914B in a similar manner as described above with respect to FIGS. 6A and 6B (e.g., using a gap-controlled heated nip roller) to form the dual-plenum platform 902.

Furthermore, the first surface 910 of the platform 902 can include first apertures 922A formed therethrough that can be used for patient warming/cooling, and the third surface 960 can include second apertures 922B formed therein that can be used for patient transfer (e.g., via a fluid-assisted pallet to reduce friction).

In such embodiments, the patient transfer and patient warming/cooling operations can be completely independent from one another, such that patient transfer and patient warming/cooling can be provided separately or simultaneously, depending on the need for a given patient or procedure.

For patient warming applications, the fluid (e.g. air) may be heated by a variety of means. For example, in some embodiments, an electrical resistance heater can be employed. One such heated forced air convection unit is described in U.S. Pat. No. 7,014,431, which is incorporated herein by reference.

For patient cooling applications, the fluid (e.g. air) may be cooled via an electrical refrigeration unit much like a modern air conditioner. Alternatively, the air may be cooled by expansion of pressurized air.

Figure 11:
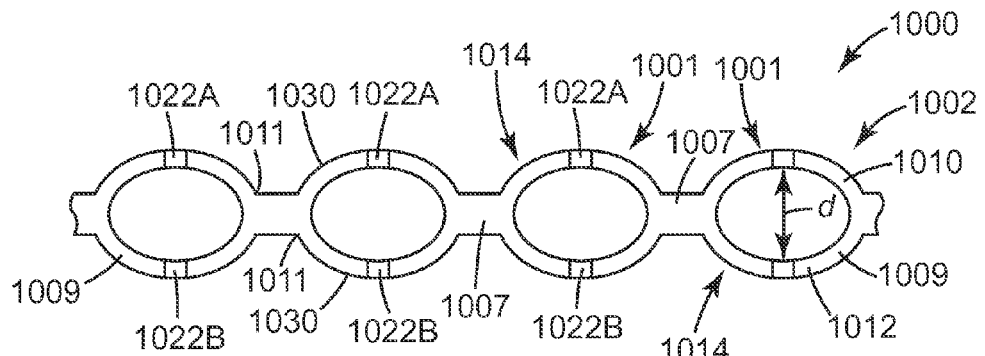
FIG. 11 is a schematic cross-sectional view of a patient support system according to another embodiment of the present disclosure.

FIG. 11 illustrates at least a portion of a patient support system 1000 according to another embodiment of the present disclosure, wherein like numerals represent like elements. The patient support system 1000 shares many of the same elements and features described above with reference to the illustrated embodiments of FIGS. 1-3, and potentially others. Accordingly, elements and features corresponding to elements and features in the illustrated embodiments of FIGS. 1-3 are provided with the same reference numerals in the 1000 series. Reference is made to the descriptions above, for example, accompanying FIGS. 1-3, for a more complete description of the features and elements (and alternatives to such features and elements) of the embodiment illustrated in FIG. 11.

The patient support system 1000 can be configured for patient transfer and/or patient thermal control and includes a platform 1002 formed by a plurality of rigid, semi-rigid or flexible tubes 1001 (or combinations thereof) that are arranged side-by-side and extend into and out of the plane of the page of FIG. 11. As shown in FIG. 11, the tubes 1001 can be coupled together by a series of spacer elements 1007, which can be flexible, semi-rigid, or rigid. In embodiments in which the tubes 1001 are flexible, the tubes 1001 can still be non-inflatable. Flexible tubes 1001 can facilitate rolling or folding the platform 1002, for example, for packaging or handling; however, semi-rigid or rigid tubes 1001 may provide additional structural integrity and a more expedient creation of a fluid pallet and/or thermal control of a patient. In embodiments employing flexible spacer elements 1007, the spacer elements 1007 can facilitate folding or rolling of the platform 1002, even if the tubes 1001 themselves are not particularly flexible. By way of example only, such flexible spacer elements 1007 can be formed of a flexible elastomer or a thin, flexible polymer (e.g., a polyolefin), other suitable elastomers or polymers, or combinations thereof.

As shown in FIG. 11, the platform 1002 includes a first surface 1010 and a second surface 1012 that can each be at least partially defined by a surface of the tubes 1001 and/or the spacer elements 1007, and the tubes 1001 can be hollow. The tubes 1001 are shown by way of example only in FIG. 11 as having a generally ellipsoidal or oblong cross-sectional shape. As a result, the first surface 1010 and the second surface 1012 can be separated a variable distance d apart. For example, the distance d can vary, as shown, with the transverse dimension of the tubes 1001, can increase toward a horizontal center of each tube 1001, and can decrease toward the spacer elements 1007. The hollow cross-sectional shape of each tube 1001 provides a chamber or plenum 1020 between the first surface 1010 and the second surface 1012. Alternatively, in some embodiments, the spacer elements 1007 can also be hollow, such that the platform 1002 includes one continuous plenum 1020 formed by the tubes 1001 and spacer elements 1007. In some embodiments, a combination of plenums 1020 formed by a single tube 1001 and plenums 1020 formed by two or more tubes 1001 and/or spacer elements 1007 can be employed.

In addition, at least a portion of sides or walls 1009 of the tubes 1001 can function as supporting structures 1014 of the patient support system 1000. As a result, the platform 1002 of FIG. 11 may include supporting structures 1014 that are integrally formed with the first surface 1010 and the second surface 1012. As a result of the supporting structures 1014 being integrally formed with the first surface 1012 and the second surface 1012, the tubes 1001 can be provided by a facile manufacturing method such as extrusion and/or molding. Furthermore, in some embodiments, the spacer elements 1007 can be integrally formed with the tubes 1001, as shown in FIG. 11. Even in embodiments in which the spacer elements 1007 are formed of a different material than one or more of the tubes 1001, the platform 1002 as a whole (e.g., including the spacer elements 1007) can be provided by a facile manufacturing method such as extrusion (e.g., co-extrusion), and/or molding.

The tubes 1001 (e.g., when the tubes 1001 are formed of a flexible material) can also include additional internal supporting structures, such as any of those described herein, which can provide the necessary support and fluid pathway definition, either in lieu of, or in addition to the supporting structures 1014 shown in FIG. 11.

Figure 12:
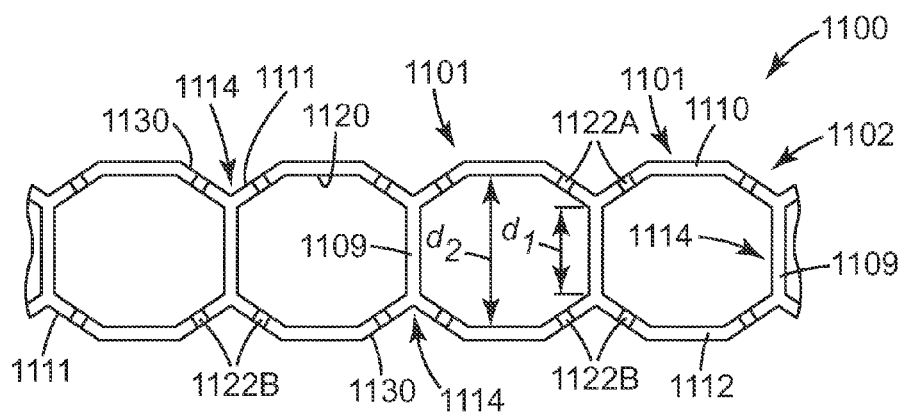
FIG. 12 is a schematic cross-sectional view of a patient support system according to another embodiment of the present disclosure.

It should be understood that the ellipsoidal or oblong cross-sectional shape of the tubes 1001 is shown by way of example only, and a variety of other hollow cross-sectional shapes can be employed, including, but not limited to, at least one of circles, triangles, trapezoids, squares, rectangles, diamonds, polygons, other suitable cross-sectional shapes, and combinations thereof. For example, tubes of polygonal cross-sectional shapes are shown in FIG. 12 and described below. Similarly, it should be understood that the spacer elements 1007 are shown in FIG. 11 by way of example only, but the platform 1002 can instead include the tubes 1001 coupled directly to one another or integrally formed together, rather than being coupled together via spacer elements 1007. In such embodiments, the platform 1002 can include a plurality of plenums 1020, each formed by a single tube 1001, one plenum 1020 formed by a plurality of tubes 1001, or a combination thereof.

As shown in FIG. 11, the spacer elements 1007 of the platform 1002 are less thick from top to bottom (i.e., have a smaller dimension in the vertical direction of FIG. 11) than the tubes 1001. In addition, the spacer elements 1007 are positioned centrally with respect to a vertical center of the tubes 1001. As a result, the first surface 1010 and the second surface 1012 each include a plurality of recesses 1011 defined by at least a portion of the tube walls 1009 and/or the spacer elements 1007 (if employed). In embodiments that do not include the spacer elements 1007, the recesses 1011 can be formed between adjacent tubes 1001, at least partially due to the cross-sectional shape of the tubes 1001.

The tubes 1001 can be formed to be continuous or discrete in the machine direction (i.e., the direction that extends into and out of the page of FIG. 11), such that the tubes 1001 can be provided as long tubes, each having a length that extends along the entire length of the platform 1002; can be provided as beads (e.g., that can be fluidly connected along the width and/or length of the platform 1002), each having a short length in the machine direction; or a combination thereof.

Similar to some of the embodiments described above, the first surface 1010 of the platform 1002 can include first apertures 1022A formed therethrough that can be used for patient thermal control, and the second surface 1012 can include second apertures 1022B formed therein that can be used for patient transfer. The tubes 1001 are each shown by way of example only as including one or more first apertures 1022A along its machine direction length, as well as one or more second apertures 1022B along its machine direction length. However, it should be understood that in some embodiments, each tube 1001 can instead include only first apertures 1022A, only second apertures 1022B, or the first and second apertures 1022A and 1022B can vary or alternate along its machine direction length, such that both would not be visible in the same cross-section. Furthermore, similar to other embodiments described above, any of the first apertures 1022A and the second apertures 1022B can include one or more valves that can be activated to open, for example, only when desired or under certain conditions.

The first and second apertures 1022A and 1022B are both shown as being formed through the top center and bottom center of each of the tubes 1001. However, it should be understood that the first apertures 1022A and/or the second apertures 1022B can instead be formed toward the recesses 1011 formed between adjacent tubes 1001. In such embodiments, the structure(s) that define each recess 1011 can also define at least a portion of a skirt 1030, such that each recess 1011 can function as a skirt 1030 to retain fluid and/or direct fluid flow out of the apertures 1022A or 1022B, for example, to inhibit the fluid from immediately escaping to the sides of the platform 1002. An example of such a configuration is shown in FIG. 12 and described below.

FIG. 12 illustrates at least a portion of a patient support system 1100 according to another embodiment of the present disclosure, wherein like numerals represent like elements. The patient support system 1100 shares many of the same elements and features described above with reference to the illustrated embodiments of FIGS. 1-3, 11, and potentially others. Accordingly, elements and features corresponding to elements and features in the illustrated embodiments of FIGS. 1-3 and 11 are provided with the same reference numerals in the 1100 series. Reference is made to the descriptions above, for example, accompanying FIGS. 1-3 and 11, for a more complete description of the features and elements (and alternatives to such features and elements) of the embodiment illustrated in FIG. 12.

The patient support system 1100 can be configured for patient transfer and/or patient thermal control and includes a platform 1102 formed by a plurality of rigid, semi-rigid or flexible tubes 1101 (or combinations thereof) that are arranged side-by-side and extend into and out of the plane of the page of FIG. 12. As shown in FIG. 12, the tubes 1101 can be coupled together, and in some embodiments (as shown), can be integrally formed with one another. Unlike the platform 1002 of FIG. 11, the platform 1102 does not include spacer elements between adjacent tubes 1101.

As shown in FIG. 12, the platform 1102 includes a first surface 1110 and a second surface 1112 that can each be defined by the tubes 1101, and the tubes 1101 can be hollow. The tubes 1101 are shown by way of example only in FIG. 12 as having a polygonal cross-sectional shape, and particularly, a non-uniform octagonal shape in which the vertical sides, along which the tubes 1101 are coupled to an adjacent tube 1101, are the longest. Other cross-sectional shapes are possible and within the spirit and scope of the present disclosure, however. Because of the illustrated octagonal shape of the tubes 1101, the first surface 1110 and the second surface 1112 can be separated a variable distance apart that ranges from $d_1$ at the sides of each tube 1101 to $d_2$ at the horizontal center of each tube 1101.

In addition, at least a portion of sides or walls 1109 of the tubes 1101 can function as supporting structures 1114 of the patient support system 1100. As a result, the platform 1102 of FIG. 12 may include supporting structures 1114 that are integrally formed with the first surface 1110 and the second surface 1112. As a result, the platform 1102 can be provided by a facile manufacturing method such as extrusion and/or molding.

Alternatively, or in addition, internal supporting structure(s) may be provided, as described above with reference to FIG. 11. That is, one or more supporting structures may be provided within the tubes 1101, in addition to, or in lieu of, the supporting structures 1114. Because of the individual octagonal shapes in the cross-section of the platform 1102, the platform 1102 is described as including a plurality or series of tubes 1101. However, the platform 1102 can simply be described by the first surface 1110, the second surface 1112, and the supporting structures 1114, similar to the platform 202 of FIG. 3, for example.

The hollow cross-sectional shape of each tube 1101 provides a chamber or plenum 1120 between the first surface 1110 and the second surface 1112. Alternatively, in some embodiments, the supporting structures 1114 can include one or more openings formed therein, such that one continuous plenum 1120 can be formed in the platform 1102. In some embodiments, a combination of plenums 1120 formed by a single tube 1101 and plenums 1120 formed by two or more tubes 1101 can be employed.

As shown in FIG. 12, because of the cross-sectional shape of the tubes 1101, the platform 1102 varies in height along its width, and the first surface 1110 and the second surface 1112 each include a plurality of recesses 1111 defined by at least a portion of the tube walls 1109.

Similar to some of the embodiments described above, the first surface 1110 of the platform 1102 can include first apertures 1122A formed therethrough that can be used for patient thermal control, and the second surface 1112 can include second apertures 1122B formed therein that can be used for patient transfer. The tubes 1101 are each shown by way of example only as including one or more first apertures 1122A along its machine direction length, as well as one or more second apertures 1122B along its machine direction length. However, it should be understood that in some embodiments, each tube 1101 can instead include only first apertures 1122A, only second apertures 1122B, or the first and second apertures 1122A and 1122B can vary or alternate along its machine direction length, such that both would not be visible in the same cross-section. Furthermore, similar to other embodiments described above, any of the first apertures 1122A and the second apertures 1122B can include one or more valves that can be activated to open, for example, only when desired or under certain conditions.

The first and second apertures 1122A and 1122B are shown as being formed in the recesses 1111, or in the recessed regions of the first and second surfaces 1110 and 1112. As such, the walls 1109 of the tubes 1101 that define each recess 1111 can also define at least a portion of a skirt 1130, such that each recessed area of the surfaces 1110 and/or 1112 can function as a skirt 1130 to retain the fluid and/or direct fluid flow out of the apertures 1122A or 1122B, for example, to inhibit the fluid from immediately escaping to the sides of the platform 1102. As a result, the first surface 1110 and/or the second surface 1112 can include or define the skirt(s) 1130 of the patient support system 1100 used to control and/or direct fluid flow.

The tubes 1101 can be formed to be continuous or discrete in the machine direction (i.e., the direction that extends into and out of the page of FIG. 12), such that the tubes 1101 can be provided as long tubes, each having a length that extends along the entire length of the platform 1102; can be provided as beads (e.g., that can be fluidly connected along the width and/or length of the platform 1102), each having a short length in the machine direction; or a combination thereof.

Figure 13:
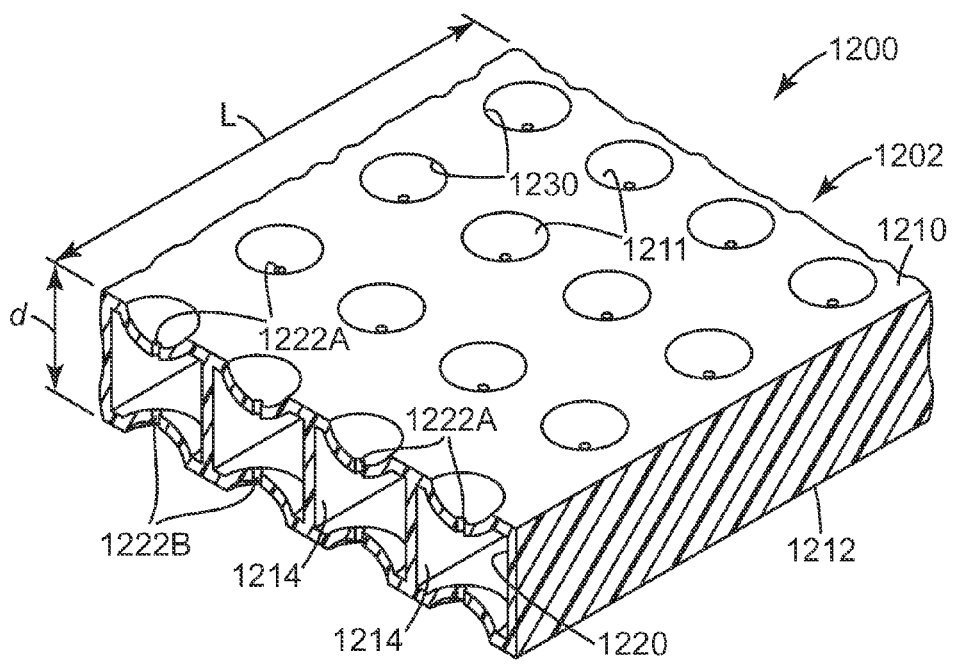
FIG. 13 is a partial perspective view, with two sides shown in cross-section, of a patient support system according to another embodiment of the present disclosure.

FIG. 13 illustrates at least a portion of a patient support system 1200 according to another embodiment of the present disclosure, wherein like numerals represent like elements. The patient support system 1200 shares many of the same elements and features described above with reference to the illustrated embodiments of FIGS. 1-3, 11, 12, and potentially others. Accordingly, elements and features corresponding to elements and features in the illustrated embodiments of FIGS. 1-3, 11 and 12 are provided with the same reference numerals in the 1200 series. Reference is made to the descriptions above, for example, accompanying FIGS. 1-3, 11 and 12, for a more complete description of the features and elements (and alternatives to such features and elements) of the embodiment illustrated in FIG. 13.

The patient support system 1200 can be configured for patient transfer and/or patient thermal control and includes a platform 1202 that is formed substantially the same as the platform 202 of FIG. 3 (shown without support projections for simplicity). That is, the platform 1202 includes a first (top) surface 1210 and a second (bottom) surface 1212 positioned substantially parallel to the first surface 1210 and separated from the first surface 1210 by a distance d that varies because of dimples or depressions that are formed in the first and second surfaces 1210 and 1212, which are described in greater detail below. One or more chambers or plenums 1220 are formed between the first surface 1210 and the second surface 1212. As shown in FIG. 13, each of the first surface 1210 and the second surface 1212 include a major surface that extends in the direction of its length and width and which, in some portions, faces the major surface of the other surface.

As shown in FIG. 13, the patient support system 1200 can further include supporting structures 1214 that can extend at least partially across the distance d or gap between the first surface 1210 and the second surface 1212. In addition, the supporting structures 1214 are shown as being coupled to and integrally formed with both the first surface 1210 and the second surface 1212, even though this need not be the case. As described above, such a platform 1202 can be made according to facile manufacturing methods, such as extrusion and/or molding.

The plenum(s) 1220 can be at least partially defined by the first surface 1210, the second surface 1212, and the supporting structures 1214. The supporting structures 1214 can include an x- and/or y-dimension similar to the supporting structures 114 of FIG. 1 and can extend along the length L of the platform 1202 (e.g., "columnar"), essentially dividing the plenum 1220 into a plurality of plenums 1220. In other embodiments, as described and illustrated in embodiments above, the supporting structures 1214 can instead be "post-like" or have a length that does not extend along the entire length L of the platform 1202 (e.g., like a series of short or partial-length walls) such that they define one larger plenum 1220. In some embodiments, a combination of columnar, post-like, and or "partial wall" supporting structures 1214 can be employed.

The patient support system 1200 can be configured for use in patient transfer and/or patient thermal control applications, and the first surface 1210 can include first apertures 1222A formed therethrough, for example, that can be used for patient warming/cooling, and the second surface 1212 can include second apertures 1222B formed therein that can be used for patient transfer, for example. As described above, the apertures 1222 can be open or valved. By way of example only, the supporting structures 1214 and the apertures 1222 are shown as being arranged in a regular and repeating array; however, as described above, this need not be the case.

The difference between the platform 1202 of FIG. 13 and the platform 202 of FIG. 3 is that the platform 1202 of FIG. 13 includes a plurality of depressions, dimples, recesses 1211, or the like, formed into the first surface 1210 and the second surface 1212, and the apertures 1222 are formed in the recesses 1211, particularly, at the center of the recesses 1211, although this need not be the case. In some embodiments, only the first surface 1210 or only the second surface 1212 includes the recesses 1211.

The platform 1202 can be formed, for example, by an extrusion process, similar to that described above, followed by (e.g., directly followed by, so that the platform 1202 is still warm from the extrusion process) being passed through an embossing roll (e.g., between nip rollers) to emboss the recesses 1211 into the first surface 1210 and/or the second surface 1212. The embossing roll(s) can also include means for puncturing or slitting the first surface 1210 and/or the second surface 1212, such that the apertures 1222 are formed in the recesses 1211 and formed simultaneously therewith.

Because of the recesses 1211, the first and second surfaces 1210 and 1212 can have a wavy or dimpled profile, as shown in the sectioned surface of the platform 1202 in FIG. 13. The recesses 1211 (and the apertures 1222) are shown as being regularly arranged on the platform 1202 of FIG. 13, but this need not be the case. Rather, any desired embossing pattern (regular, irregular, random, or a combination thereof) can be employed to form any desired pattern or arrangement of recesses 1211 and apertures 1222. Furthermore, embossing is described by way of example only; however, it should be understood that other suitable processes for forming the recesses 1211 and/or the apertures 1222 can be employed.

As mentioned above, the first and second apertures 1222A and 1222B are shown as being formed in the recesses 1211, or in the recessed regions of the first and second surfaces 1210 and 1212. As such, the structure(s) and/or the surfaces(s) that defines each recess 1211 can also define at least a portion of a skirt 1230 that can function to retain the fluid and/or direct fluid flow out of the apertures 1222A or 1222B, for example, to inhibit the fluid from immediately escaping to the sides of the platform 1202. As a result, the first surface 1210 and/or the second surface 1212 can include or define the skirt(s) 1230 of the patient support system 1200 used to control and/or direct fluid flow.

While each of the patient support systems 100, 200, 300, 400, 500, 600, 700, 800, 900, 1000, 1100 and 1200 are described separately above, it should be understood that any combination of any of the patient support systems described herein can be combined as necessary for a particular application.

As can be appreciated by one of ordinary skill in the art, any of the above patient support systems 100, 200, 300, 400, 500, 600, 700, 800, 900, 1000, 1100, 1200 can be employed for a variety of applications, including for patient transfer and/or patient thermal control applications.

For example, any of the above patient support systems 100, 200, 300, 400, 500, 600, 700, 800, 900, 1000, 1100, 1200 can be used to transfer a patient by moving fluid into the plenum(s) 120, 220, 320, 420, 520, 620, 720, 820, 920, 1020, 1120, 1220 to fill the plenum(s) 120, 220, 320, 420, 520, 620, 720, 820, 920, 1020, 1120, 1220 without inflating the platform 102, 202, 302, 402, 502, 602, 702, 802, 902, 1020, 1120, 1220; and moving fluid out the apertures (e.g., the second apertures) 122, 222, 322, 422, 522, 622, 722, 822, 922, 1022, 1122, 1222 to form a fluid pallet adjacent the second surface 112, 212, 312, 512, 612, 712, 1012, 1112, 1212 or the third surface 460, 860, 960. Such methods can further include providing a patient positioned atop the first surface 110, 210, 310, 410, 510, 610, 710, 810, 910, 1010, 1110, 1210 of the platform 102, 202, 302, 402, 502, 602, 702, 802, 902, 1002, 1102, 1202, and transferring the patient on the platform 102, 202, 302, 402, 502, 602, 702, 802, 902, 1002, 1102, 1202 via the fluid pallet.

By way of further example, any of the above patient support systems 100, 200, 300, 400, 500, 600, 700, 800, 900, 1000, 1100, 1200 can be used to warm a patient by moving a heated fluid into the plenum(s) 120, 220, 320, 420, 520, 620, 720, 820, 920, 1020, 1120, 1220 and out the apertures (e.g., the first apertures) 122, 222, 322, 422, 522, 622, 722, 822, 922, 1022, 1122, 1222 to convectively warm a patient positioned atop the first surface 110, 210, 310, 410, 510, 610, 710, 810, 910, 1010, 1110, 1210 of the platform 102, 202, 302, 402, 502, 602, 702, 802, 902, 1002, 1102, 1202.

The following working example is intended to be illustrative of one exemplary measurement procedure for measuring the bending strength of a platform of the present disclosure, and is not intended to be limiting.

EMBODIMENTS

Embodiment 1 is a patient support system comprising:
a non-inflatable and self-supporting platform comprising:
  a first surface,
  a second surface positioned substantially parallel to the first surface and separated from the first surface by a distance,
  a plurality of supporting structures that extends at least partially across the distance between the first surface and the second surface, the plurality of supporting structures being coupled to at least one of the first surface and the second surface,
  a plenum defined at least partially by the first surface, the second surface, and the plurality of supporting structures, and
  a plurality of apertures formed through at least a portion of at least one of the first surface and the second surface and in fluid communication with the plenum; and
a fluid source fluidly coupled to the plenum, the fluid source being a positive pressure fluid source configured to move fluid from the fluid source into the plenum and out the plurality of apertures.

Embodiment 2 is a method for transferring a patient, the method comprising:
providing a patient support system comprising a non-inflatable and self-supporting platform comprising:
  a first surface,
  a second surface positioned substantially parallel to the first surface and separated from the first surface by a distance,
  a plurality of supporting structures that extend at least partially across the distance between the first surface and the second surface, the plurality of supporting structures being coupled to at least one of the first surface and the second surface,
  a plenum defined at least partially by the first surface, the second surface, and the plurality of supporting structures, and
  a plurality of apertures formed through at least a portion of the second surface and in fluid communication with the plenum to allow fluid to exit the plenum via the plurality of apertures;
moving fluid into the plenum to fill the plenum without inflating the platform more than 200% from its nonpressured state; and
moving fluid out the plurality of apertures.

Embodiment 3 is a method for controlling the temperature of a patient, the method comprising:
providing a patient support system comprising a non-inflatable and self-supporting platform comprising:
  a first surface,
  a second surface positioned substantially parallel to the first surface and separated from the first surface by a distance,
  a plurality of supporting structures that extend at least partially across the distance between the first surface and the second surface, the plurality of supporting structures being coupled to at least one of the first surface and the second surface,
  a plenum defined at least partially by the first surface, the second surface, and the plurality of supporting structures, and
  a plurality of apertures formed through at least a portion of the first surface and in fluid communication with the plenum to allow fluid to exit the plenum via the plurality of apertures; and
moving a temperature-controlled fluid into the plenum and out the plurality of apertures.

Embodiment 4 is the method of embodiment 2 or 3, wherein the patient support system further comprises a fluid source fluidly coupled to the plenum of the platform, the fluid source being a positive pressure fluid source configured to move fluid from the fluid source into the plenum and out the plurality of apertures.

Embodiment 5 is the patient support system of embodiment 1 or the method of any of embodiments 2-4, wherein at least a portion of the first surface and at least a portion of the second surface are coupled together.

Embodiment 6 is the patient support system of embodiment 1 or 5 or the method of any of embodiments 2-5, wherein the first surface, the second surface and the plurality of supporting structures are integrally formed.

Embodiment 7 is the patient support system of any of embodiments 1 and 5-6 or the method of any of embodiments 2-6, wherein at least a portion of the platform is formed by a profile extrusion process.

Embodiment 8 is the patient support system of any of embodiments 1 and 5-7 or the method of any of embodiments 2-7, wherein the platform is provided in a rolled or folded form.

Embodiment 9 is the patient support system of any of embodiments 1 and 5-8 or the method of any of embodiments 2-8, wherein the platform is one of a plurality of platforms that are provided in a stacked configuration.

Embodiment 10 is the patient support system of any of embodiments 1 and 5-9 or the method of any of embodiments 2-9, wherein the platform is non-collapsible.

Embodiment 11 is the patient support system or method of embodiment 10, wherein the first surface and the second surface are spaced apart under an externally applied load of up to about 15 kPa.

Embodiment 12 is the patient support system of any of embodiments 1 and 5-11 or the method of any of embodiments 2-11, wherein at least a portion of at least one of the first surface and the second surface is flexible.

Embodiment 13 is the patient support system of any of embodiments 1 and 5-12 or the method of any of embodiments 2-12, wherein at least a portion of at least one of the first surface and the second surface is rigid.

Embodiment 14 is the patient support system of any of embodiments 1 and 5-13 or the method of any of embodiments 2-13, wherein the distance separating the first surface and the second surface is variable.

Embodiment 15 is the patient support system of any of embodiments 1 and 5-14 or the method of any of embodiments 4-14, wherein the plurality of supporting structures at least partially define a plurality of fluid channels in the plenum that are fluidly coupled to the fluid source via a manifold.

Embodiment 16 is the patient support system of any of embodiments 1 and 5-15 or the method of any of embodiments 4-15, wherein the plenum is fluidly coupled to a manifold positioned in fluid communication with the fluid source.

Embodiment 17 is the patient support system of any of embodiments 1 and 5-16 or the method of any of embodiments 2-16, further comprising a fluid path in the platform, the fluid path defined at least partially by an inlet to the plenum, the plenum, and the plurality of apertures.

Embodiment 18 is the patient support system of any of embodiments 1 and 5-17 or the method of any of embodiments 2-17, wherein the plenum includes a fluid pressure at the inlet of no greater than about 35 kPa.

Embodiment 19 is the patient support system of any of embodiments 1 and 5-18 or the method of any of embodiments 2-18, wherein the plenum includes a fluid pressure at the inlet of at least about 3 kPa.

Embodiment 20 is the patient support system of any of embodiments 1 and 5-19 or the method of any of embodiments 2-19, wherein the plurality of supporting structures are integrally formed with at least one of the first surface and the second surface.

Embodiment 21 is the patient support system of any of embodiments 1 and 5-20 or the method of any of embodiments 2-20, wherein the plurality of supporting structures includes a plurality of hooks Embodiment 22 is the patient support system or method of embodiment 21, wherein each of the plurality of hooks includes a stem and a cap coupled to the stem, and wherein the plurality of hooks are integrally formed with the second surface, such that the stem extends from the second surface toward the first surface and a top surface of the cap is configured to face the first surface.

Embodiment 23 is the patient support system or method of embodiment 21 or 22, wherein each of the plurality of hooks is columnar and further extends in a direction parallel to a major surface of at least one of the first surface and the second surface.

Embodiment 24 is the patient support system of any of embodiments 1 and 5-23 or the method of any of embodiments 2-23, wherein the plurality of supporting structures is a first plurality of supporting structures coupled to the first surface, and further comprising a second plurality of supporting structures coupled to the second surface and positioned to extend at least partially across the distance between the first surface and the second surface.

Embodiment 25 is the patient support system or method of embodiment 24, wherein the first plurality of supporting structures includes a first plurality of interlocking hooks and the second plurality of supporting structures includes a second plurality of interlocking hooks, and wherein the first plurality of interlocking hooks are interlocked with the second plurality of interlocking hooks.

Embodiment 26 is the patient support system of any of embodiments 1 and 5-25 or the method of any of embodiments 2-25, wherein at least one of the first surface and the second surface is formed at least in part of a polyolefin.

Embodiment 27 is the patient support system of any of embodiments 1 and 5-26 or the method of any of embodiments 2-26, wherein at least one of the first surface and the second surface is formed at least in part of an aliphatic polyester resin.

Embodiment 28 is the patient support system of any of embodiments 1 and 5-27 or the method of any of embodiments 2-27, wherein at least one of the first surface and the second surface includes a contact surface having a kinetic coefficient of friction of less than 0.5 when measured according to ASTM D1894-08 with the material sliding over itself.

Embodiment 29 is the patient support system of any of embodiments 1 and 5-28 or the method of any of embodiments 2-28, wherein the at least one of the first surface and the second surface in which the plurality of apertures is formed includes a first portion comprising the plurality of apertures and a second portion in which no apertures are formed.

Embodiment 30 is the patient support system or method of embodiment 29, wherein the first portion is positioned outwardly of the second portion, relative to a center of the platform.

Embodiment 31 is the patient support system or method of embodiment 29, wherein the second portion is positioned outwardly of the first portion, relative to a center of the platform.

Embodiment 32 is the patient support system of any of embodiments 1 and 5-31 or the method of any of embodiments 2-31, wherein the plurality of apertures is a first plurality of apertures formed in the first surface, and further comprising a second plurality of apertures formed in the second surface.

Embodiment 33 is the patient support system of any of embodiments 1 and 5-32 or the method of any of embodiments 2-32, wherein the first plurality of apertures is formed adjacent a periphery of the first surface, and wherein the second plurality of apertures is positioned toward the center of the second surface.

Embodiment 34 is the patient support system of any of embodiments 1 and 5-33 or the method of any of embodiments 2-33, further comprising a second plurality of supporting structures coupled to at least one of the first surface and the second surface and extending outwardly therefrom, such that the second plurality of supporting structures is exposed to ambience.

Embodiment 35 is the patient support system of any of embodiments 1 and 5-34 or the method of any of embodiments 2-34, wherein the plenum is a first plenum, the plurality of supporting structures is a first plurality of supporting structures, and the plurality of apertures is a first plurality of apertures, wherein the first plurality of apertures is formed through at least a portion of the second surface, and wherein the platform further comprises:
  a third sheet oriented substantially parallel to the first surface and opposite the second surface, the third sheet separated from the first surface by a second distance;
  a second plurality of supporting structures that extend at least partially across the second distance between the first surface and the third sheet, the second plurality of supporting structures being coupled to at least one of the first surface and the third sheet; and
  a second plenum defined at least partially by the first surface, the third sheet, and the second plurality of supporting structures.

Embodiment 36 is the patient support system or method of embodiment 35, further comprising a second plurality of apertures formed through at least a portion of the third sheet and in fluid communication with the second plenum to allow fluid to exit the second plenum via the second plurality of apertures.

Embodiment 37 is the patient support system or method of embodiment 35 or 36, wherein the second plenum is in fluid communication with a second fluid source.

Embodiment 38 is the patient support system of any of embodiments 1 and 5-37 or the method of any of embodiments 2-37, further comprising a skirt coupled to at least one of the first surface and the second surface adjacent the plurality of apertures to direct fluid exiting the plurality of apertures.

Embodiment 39 is the patient support system or method of embodiment 38, wherein the skirt is inflatable.

Embodiment 40 is the patient support system or method of embodiment 38 or 39, wherein the skirt is positioned to inhibit fluid from exiting the plurality of apertures in a direction substantially parallel to the at least one of the first surface and the second surface.

Embodiment 41 is the patient support system or method of any of embodiments 38-40, wherein the fluid source is further fluidly coupled to the skirt to move fluid into the skirt.

Embodiment 42 is the patient support system or method of any of embodiments 38-41, wherein the skirt is positioned adjacent an edge of the platform.

Embodiment 43 is the patient support system or method of any of embodiments 38-42, wherein the platform includes a first portion comprising the plurality of apertures and a second portion in which no apertures are formed, and wherein the skirt is positioned between the first portion and the second portion of the platform.

Embodiment 44 is the patient support system or method of any of embodiments 38-43, wherein the skirt is formed of a deformable material.

Embodiment 45 is the patient support system of any of embodiments 1 and 5-44 or the method of any of embodiments 2-44, wherein the first surface is adapted to face a patient, and wherein the plurality of apertures is formed in the first surface only.

Embodiment 46 is the patient support system of any of embodiments 1 and 5-45 or the method of any of embodiments 2-45, wherein the first surface is adapted to face a patient, and wherein the plurality of apertures is formed in the second surface only.

Embodiment 47 is the patient support system of any of embodiments 1 and 5-46 or the method of any of embodiments 2-46, wherein the platform includes an outer edge, and wherein the outer edge is curved toward one of the first surface or the second surface.

Embodiment 48 is the patient support system of any of embodiments 1 and 5-47 or the method of any of embodiments 2-47, wherein the distance between the first surface and the second surface is oriented along a z-axis, such that the plurality of supporting structures includes a z-dimension, and wherein at least some of the plurality of supporting structures further include at least one of an x-dimension and a y-dimension oriented orthogonally to the z-dimension.

Embodiment 49 is the patient support system of any of embodiments 1 and 5-48 or the method of any of embodiments 2-48, wherein the plurality of supporting structures further extend in a direction parallel to a major surface of at least one of the first surface and the second surface.

Embodiment 50 is the patient support system of any of embodiments 1 and 5-49 or the method of any of embodiments 2-49, further comprising a conformable body coupled to one of the first surface and the second surface to provide cushion to a patient.

Embodiment 51 is the patient support system or method of embodiment 50, wherein the first surface is adapted to face a patient, and wherein the conformable body is coupled to the first surface.

Embodiment 52 is the patient support system or method of embodiment 50 or 51, wherein the plurality of apertures is a first plurality of apertures, and wherein the conformable body further includes a second plurality of apertures positioned in fluid communication with the first plurality of apertures.

Embodiment 53 is the patient support system or method of any of embodiments 50-52, wherein the conformable body is formed of a material comprising at least one of an open cell foam, a nonwoven, a woven fabric, a knit fabric, a gel pad, and a combination thereof.

Embodiment 54 is the patient support system or method of any of embodiments 50-53, wherein the conformable body includes an antimicrobial coating.

Embodiment 55 is the patient support system or method of any of embodiments 50-54, wherein the conformable body is inflatable.

Embodiment 56 is the patient support system or method of embodiment 55, wherein the fluid source is further fluidly coupled to the conformable body.

Embodiment 57 is the patient support system of any of embodiments 1 and 5-56 or the method of any of embodiments 2-56, further comprising a liner configured to be positioned adjacent at least one of the first surface and the second surface of the platform.

Embodiment 58 is the patient support system or method of embodiment 57, wherein the liner includes a slip sheet.

Embodiment 59 is the patient support system of any of embodiments 1 and 5-58 or the method of any of embodiments 2-58, wherein at least one of the first surface and the second surface are formed of a non-absorbent material.

Embodiment 60 is the patient support system of any of embodiments 1 and 5-59 or the method of any of embodiments 2-59, wherein at least one of the first surface and the second surface include an antimicrobial coating.

Embodiment 61 is the patient support system of any of embodiments 1 and 5-60 or the method of any of embodiments 2-60, wherein the platform is one of a plurality of platform segments that are positioned in fluid communication.

Embodiment 62 is the patient support system of any of embodiments 1 and 5-61 or the method of any of embodiments 2-61, further comprising at least one handle that includes an aperture formed through the platform.

Embodiment 63 is the patient support system of any of embodiments 1 and 5-62 or the method of any of embodiments 2-62, further comprising at least one strap coupled to the platform.

Embodiment 64 is the patient support system of any of embodiments 1 and 5-63 or the method of any of embodiments 2-63, wherein the fluid comprises a temperature-controlled gas.

Embodiment 65 is the patient support system or method of embodiment 64, wherein the temperature-controlled gas comprises heated air.

Embodiment 66 is the patient support system or method of embodiment 64, wherein the temperature controlled gas comprises chilled air.

Embodiment 67 is the patient support system of any of embodiments 1 and 5-66 or the method of any of embodiments 2-66, wherein at least one of the first surface and the second surface has a three-point bending strength of at least about 5 N when tested according to ASTM D790-07 procedure B.

Embodiment 68 is the patient support system of any of embodiments 1 and 5-67 or the method of any of embodiments 2-67, further comprising a fluid blocking layer positioned adjacent at least some of the plurality of apertures to selectively block fluid flow out of the plurality of apertures.

Embodiment 69 is the method of any of embodiments 2, 4-68, further comprising:
providing a patient positioned atop the first surface of the platform; and
transferring the patient on the platform using the fluid pallet.

Embodiment 70 is the method of any of embodiments 3-68, further comprising:
providing a patient positioned atop the first surface of the platform; and
controlling the temperature of the patient with the temperature-controlled fluid exiting the plurality of apertures.

Embodiment 71 is a patient support system comprising:
a non-inflatable and self-supporting platform comprising:
a first surface, a second surface positioned substantially parallel to the first surface and separated from the first surface by a first distance,
a first plurality of supporting structures that extends at least partially across the first distance between the first surface and the second surface, the plurality of supporting structures being coupled to at least one of the first surface and the second surface,
a first plenum defined at least partially by the first surface, the second surface, and the plurality of supporting structures,
a third sheet positioned substantially parallel to the second surface and positioned opposite the first surface, the third sheet separated from the second surface by a second distance,
a second plurality of supporting structures that extends at least partially across the second distance between the second surface and the third sheet, the plurality of supporting structures being coupled to at least one of the second surface and the third sheet, and
a second plenum defined at least partially by the third sheet and the second plurality of supporting structures, and
a plurality of apertures formed through at least a portion of the third sheet and in fluid communication with the second plenum; and
a fluid source fluidly coupled to the second plenum, the fluid source being a positive pressure fluid source configured to move fluid from the fluid source into the second plenum and out the plurality of apertures.

Embodiment 72 is the patient support system of embodiment 71, further comprising a heat transfer unit fluidly coupled to the first plenum, the heat transfer unit configured to thermally control fluid in the first plenum.

Embodiment 73 is a method for controlling the temperature of a patient and transferring a patient, the method comprising:
providing a patient support system comprising a non-inflatable and self-supporting platform comprising:
a first surface,
a second surface positioned substantially parallel to the first surface and separated from the first surface by a first distance,
a first plurality of supporting structures that extends at least partially across the first distance between the first surface and the second surface, the plurality of supporting structures being coupled to at least one of the first surface and the second surface,
a first plenum defined at least partially by the first surface, the second surface, and the plurality of supporting structures,
a third sheet positioned substantially parallel to the second surface and positioned opposite the first surface, the third sheet separated from the second surface by a second distance,
a second plurality of supporting structures that extends at least partially across the second distance between the second surface and the third sheet, the plurality of supporting structures being coupled to at least one of the second surface and the third sheet, and
a second plenum defined at least partially by the third sheet and the second plurality of supporting structures, and
a plurality of apertures formed through at least a portion of the third sheet and in fluid communication with the second plenum; and
providing a temperature-controlled first fluid into the first plenum; and
moving fluid into the second plenum and out the plurality of apertures.

EXAMPLES

Example 1

Measurement of Platform Bending Strength

A platform (Corrugated Plastic Sheet, Item #10005 from Wisconsin Packaging Corp., Fort Atkinson, Wis.) was obtained, having a thickness of 6 mm, a length of 8 ft (2.4 m) and a width of 4 ft (1.2 m). This platform had plenum supporting structures integrally formed with both the top and bottom surfaces (presumably formed by profile extrusion). The supporting structures formed columns or ribs that extended in the length direction. The bending strength of this material was determined using a three-point bend test as described in American Society of Testing Materials (ASTM) test method D790-07 procedure B. The material was tested for bending strength in both major axes, i.e., the length or machine direction and the width or cross direction. Samples were die cut to a width of 20 mm and a length of 100 mm. The span length (from center of support to center of support was 80 mm). The loading nose and the support rods had a diameter of 20 mm. The support length was 205 mm. The height of the support from the base to the middle of the support rod was 110 mm. The base had a length of 300 mm and a width of 115 mm. Procedure B was used since the platform material was ductile and did not fracture. The crosshead speed was run at 21.3 mm/min. The maximum deflection load was recorded and the results are shown in Table 1 below.

TABLE 1

Three-point bend test results

| Sample Number | Max Load (N) - Machine direction | Max Load (N) - Cross direction |
|---|---|---|
| 1 | 85.57 | 33.96 |
| 2 | 94.78 | 31.19 |
| 3 | 93.16 | 39.91 |
| 4 | 74.46 | 34.04 |
| 5 | 87.38 | 31.25 |
| Mean | 87.1 | 34.1 |

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:
1. A patient transfer system comprising:
a non-inflatable, self-supporting, and non-collapsible platform comprising:
a first surface,
a second surface positioned substantially parallel to the first surface and separated from the first surface by a distance, a plurality of discrete, spaced apart supporting structures, each supporting structure extending at least partially across the distance between the first surface and the second surface, a plenum defined at least partially by the first surface, the second surface, and the plurality of supporting structures, and a plurality of apertures formed through at least a portion of at least one of the first surface and the second surface and in fluid communication with the plenum, the plurality of apertures positioned to create a fluid pallet for patient transfer; and a fluid source fluidly coupled to the plenum, the fluid source being a positive pressure fluid source configured to move fluid from the fluid source into the plenum and out the plurality of apertures to form the fluid pallet.

2. The patient transfer system of claim 1, wherein at least one of the plurality of supporting structures is coupled to at least one of the first surface and the second surface.

3. The patient transfer system claim 1, wherein at least one of the plurality of supporting structures is integrally formed with at least one of the first surface and the second surface.

4. The patient transfer system of claim 1, wherein the plenum includes a fluid pressure at an inlet of no greater than about 35 kPa.

5. The patient transfer system of claim 1, wherein the plurality of supporting structures includes a plurality of hooks.

6. The patient transfer system of claim 1, wherein the plenum is a first plenum, the plurality of supporting structures is a first plurality of supporting structures, and the plurality of apertures is a first plurality of apertures, wherein the first plurality of apertures is formed through at least a portion of the second surface, and wherein the platform further comprises:

a third surface oriented substantially parallel to the first surface and opposite the second surface, the third surface separated from the first surface by a second distance;

a second plurality of supporting structures that extend at least partially across the second distance between the first surface and the third surface, the second plurality of supporting structures being coupled to at least one of the first surface and the third surface; and a second plenum defined at least partially by the first surface, the third surface, and the second plurality of supporting structures.

7. The patient transfer system of claim 6, further comprising a second plurality of apertures formed through at least a portion of the third surface and in fluid communication with the second plenum to allow fluid to exit the second plenum via the second plurality of apertures.

8. The patient transfer system of claim 1, further comprising a liner configured to be positioned adjacent at least one of the first surface and the second surface of the platform.

9. The patient transfer system of claim 1, further comprising a fluid blocking layer positioned adjacent at least some of the plurality of apertures to selectively block fluid flow out of the plurality of apertures.

10. The patient transfer system of claim 1, wherein the platform is provided in a rolled or folded form.

11. The patient transfer system of claim 1, wherein at least a portion of at least one of the first surface and the second surface is flexible.

12. The patient transfer system of claim 1, wherein the distance separating the first surface and the second surface is variable.

13. The patient transfer system of claim 1, wherein the plurality of supporting structures is a first plurality of supporting structures coupled to the first surface, and further comprising a second plurality of supporting structures coupled to the second surface and positioned to extend at least partially across the distance between the first surface and the second surface.

14. The patient transfer system of claim 1, wherein the platform has a thickness of less than 2.5 cm.

15. The patient transfer system of claim 1, wherein at least one of the first surface and the second surface are formed of a non-absorbent material.

16. The patient transfer system of claim 1, further comprising a skirt coupled to at least one of the first surface and the second surface adjacent the plurality of apertures to direct fluid exiting the plurality of apertures.

17. The patient transfer system of claim 16, wherein the skirt is inflatable.

18. The patient transfer system of claim 1, wherein the second surface is configured to face away from a patient, and wherein the plurality of apertures are formed through at least a portion of the second surface.

19. The patient transfer system of claim 1, wherein the first surface is configured to face a patient, and wherein the plurality of apertures are formed through at least a portion of the first surface; and further comprising a transfer sheet positioned adjacent the first surface.

20. The patient transfer system of claim 1, wherein the plurality of apertures is a first plurality of apertures positioned to create a fluid pallet for patient transfer, and further comprising a second plurality of apertures formed through at least a portion of at least one of the first surface and the second surface and in fluid communication with the plenum, the second plurality of apertures positioned for temperature control of a patient.

21. The patient transfer system of claim 1, wherein at least some of the plurality of supporting structures are oriented substantially orthogonally with respect to major surfaces of the first surface and the second surface.

22. The patient transfer system of claim 1, wherein the plurality of supporting structures includes at least one of a rail, a wall, a solid tube, a hollow tube, a post, a peg, a pin, and a combination thereof.

23. The patient transfer system of claim 1, wherein at least some of the plurality of supporting structures include a major surface oriented substantially orthogonally with respect to major surfaces of the first surface and the second surface.

24. The patient transfer system of claim 1, wherein the supporting structures are spaced apart from one another in a direction substantially parallel to major surfaces of the first surface and the second surface.

25. A patient transfer system comprising:

a non-inflatable, self-supporting, and non-collapsible platform comprising:

a first surface configured to face a patient, a second surface positioned substantially parallel to the first surface and separated from the first surface by a distance, a plurality of supporting structures that extends at least partially across the distance between the first surface and the second surface, a plenum defined at least partially by the first surface, the second surface, and the plurality of supporting structures, a plurality of apertures formed through at least a portion of the first surface and in fluid communication with the plenum, the plurality of apertures positioned to create a fluid pallet for patient transfer;

a transfer sheet positioned adjacent the first surface of the platform; and a fluid source fluidly coupled to the plenum, the fluid source being a positive pressure fluid source configured to move fluid from the fluid source into the plenum and out the plurality of apertures to form the fluid pallet.

26. A method for transferring a patient, the method comprising:

providing a patient transfer system comprising a non-inflatable, self-supporting, and non-collapsible platform comprising:

a first surface, a second surface positioned substantially parallel to the first surface and separated from the first surface by a distance, a plurality of discrete, spaced apart supporting structures, each supporting structure extending at least partially across the distance between the first surface and the second surface, a plenum defined at least partially by the first surface, the second surface, and the plurality of supporting structures, and a plurality of apertures formed through at least a portion of at least one of the first surface and the second surface and in fluid communication with the plenum to allow fluid to exit the plenum via the plurality of apertures;

moving fluid into the plenum to fill the plenum without inflating the platform more than 200% from its nonpressured state; and moving fluid out the plurality of apertures to form a fluid pallet.

27. The method of claim 26, further comprising moving a temperature-controlled fluid into the plenum and out the plurality of apertures.

28. The method of claim 27, further comprising:

providing a patient positioned atop the first surface of the platform; and controlling the temperature of the patient with the temperature-controlled fluid exiting the plurality of apertures.

29. The method of claim 26, wherein the patient transfer system further comprises a fluid source fluidly coupled to the plenum of the platform, the fluid source being a positive pressure fluid source configured to move fluid from the fluid source into the plenum and out the plurality of apertures.

30. The method of claim 26, further comprising:

providing a patient positioned atop the first surface of the platform; and transferring the patient on the platform using the fluid pallet.

* * * * *